(12) United States Patent
Yamato

(10) Patent No.: US 6,974,582 B2
(45) Date of Patent: Dec. 13, 2005

(54) COSMETIC COMPOSITION

(75) Inventor: Naoya Yamato, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/155,776

(22) Filed: May 28, 2002

(65) Prior Publication Data

US 2003/0124155 A1 Jul. 3, 2003

(30) Foreign Application Priority Data

Jun. 6, 2001 (JP) ........................................ 2001-171269
Nov. 1, 2001 (JP) ........................................ 2001-336884

(51) Int. Cl.$^7$ ............................................... A61K 7/00
(52) U.S. Cl. ..................................... 424/401; 424/70.1
(58) Field of Search ............................... 424/401, 70.1

(56) References Cited

FOREIGN PATENT DOCUMENTS

| JP | 11-228348 | * | 8/1999 |
| JP | 11-228527 | * | 8/1999 |
| WO | WO 00/02526 | | 1/2000 |
| WO | WO 01/74305 A1 | | 10/2001 |

OTHER PUBLICATIONS

Patent Abstracts of Japan, Masumi Ogawa, "Long–Chain Acylarginine Crystal and its Production", JP11228527, Aug. 24, 1999.

Patent Abstracts of Japan, Masahito Saito, "Moisture Retaining Cosmetic", JP2000204015, Jul. 25, 2000.

Patent Abstracts of Japan, Eishin Takanabe, "Toilet Water", JP05229928, Sep. 7, 1993.

Patent Abstracts of Japan, Yoshiro Onda, "Raw Material Substance for Cosmetic", JP63218701, Sep. 12, 1988.

*The Encyclopedia of Chemistry*, Third Ed., C.A. Hampel et al., Eds., Van Nostrand Reinhold Company, New York, pp. 687–689 (1973).

*Kirk–Othmer, Encyclopedia of Chemical Technology*, Fourth Ed., Wiley–Interscience, New York, vol. 19, pp. 886–888 (1996).

* cited by examiner

Primary Examiner—Gary Kunz
Assistant Examiner—Konata M. George
(74) Attorney, Agent, or Firm—Oblon, Spivak, McClelland, Maier & Neustadt, P.C.

(57) ABSTRACT

Herein is disclosed a cosmetic composition comprising, as active ingredients, one or more members selected from the group consisting of mono-$N^\alpha$-acylarginines and cosmetic powders whose surfaces have been treated with a mono-$N^\alpha$-acylarginine (Ingredient A) and one or more members selected from the group consisting of water-soluble polymers and alcohol-soluble polymers (Ingredient B), which cosmetic composition is excellent in conditioning effects such as moist feeling and voluminous feeling in the case of hair cosmetics and excellent in feelings upon use such as smoothening property and moist feeling without sticky feeling and occlusive feeling in the case of skin cosmetics.

19 Claims, 12 Drawing Sheets

COSMETIC COMPOSITION

BACKGROUND OF THE INVENTION

1. Technical Field of the Invention

The present invention relates to a cosmetic composition, more particularly to a cosmetic composition comprising, as active ingredients, one or more members selected from the group consisting of mono-$N^\alpha$-acylarginines and cosmetic powders whose surfaces have been treated with a mono-$N^\alpha$-acylarginine (Ingredient A) and one or more members selected from the group consisting of water-soluble polymers and alcohol-soluble polymers (Ingredient B).

The cosmetic composition of the present invention is excellent in conditioning effects such as moist feeling and voluminous feeling for the hair and is excellent in feelings upon use such as smoothening property and moist feeling without sticky feeling and occlusive feeling for the skin.

2. Related Art

In hair cosmetics such as hair detergent composition, cationic polymers or amphoteric polymers are widely used for imparting conditioning properties such as prevention of tangling of hair upon hair washing. However, since these polymers have to be incorporated in a large amount for providing sufficient conditioning properties, there is the problem that there arises, after drying the washed hair, dry and rough feeling in the hair or no sufficient voluminous feeing is attained, so that feelings upon use are poor. Moreover, for the purpose of imparting styling property mainly to the hair, an anionic polymer or nonionic polymer such as an acrylic resin alkanolamine solution, polyvinyl alcohol or the like is widely used, but these polymers are excellent in providing styling property but are unsatisfactory in view of providing conditioning property.

Furthermore, for the purpose of adjusting the viscosity of various cosmetics, stabilizing the form thereof, or providing spreadability (thixotropic property) thereof upon application, an anionic polymer or nonionic polymer such as carboxyvinyl polymer, carboxymethyl cellulose, hydroxypropylmethyl cellulose, Cyamoposis gum (i.e., guar gum) or the like is widely used. These polymers impart the above excellent functions to various cosmetics, but, as for the skin, they exhibit sticky feeling and occlusive feeling and are not excellent in feelings upon use such as smoothening property, moist feeling and the like, and as for the hair, they are not satisfactory in providing conditioning effects, since they impart dry and rough feeling and insufficient voluminous feeling, and the like.

For the purpose of enhancing smoothening property upon application of a skin cosmetic, $N^\epsilon$-lauroyl-L-lysine is sometimes incorporated. However, feelings upon use are not sufficiently excellent since satisfactory moist feeling is not attained for the skin, and sticky feeling and occlusive feeling are provided.

In Japanese Patent Application Laid-Open (Kokai) No. 228348/1999 is disclosed a cosmetic composition comprising one or more members selected from mono-$N^\alpha$-long chain-acylarginines or a powder whose surface has been treated with a mono-$N^\alpha$-long chain-acylarginine, which is excellent in providing conditioning effects such as moist feeling and settlement of the hair and also excellent in touch feeling such as non-strained feeling for the skin. However, satisfactory moist feeling for the hair and skin cannot be attained by the composition of the invention alone, and thus the composition is not sufficiently excellent in feelings upon use.

SUMMARY OF THE INVENTION

[Problems to Be Solved By the Invention]

It is an object of the present invention to provide a cosmetic composition which is excellent in providing conditioning effects such as moist feeling and voluminous feeling upon the hair being washed and dried, for the hair, and is excellent in feelings upon use such as smoothening property, moist feeling and the like, without sticky feeling and occlusive feeling, for the skin.

[Means to Solve the Problems]

The present inventor has conducted extensive and intensive studies with a view to attaining the above-mentioned object, and found, as a result, that it can be attained by the concurrent use or the use in combination of one or more members selected from the group consisting of mono-$N^\alpha$-acylarginines and cosmetic powders whose surfaces have been treated with a mono-$N^\alpha$-acylarginine and one or more members selected from the group consisting of water-soluble polymers and alcohol-soluble polymers. The present invention has been completed on the basis of these findings.

Accordingly, the present invention relates to a cosmetic composition comprising, as active ingredients, one or more members selected from the group consisting of mono-$N^\alpha$-acylarginines and cosmetic powders whose surfaces have been treated with a mono-$N^\alpha$-acylarginine (Ingredient A) and one or more members selected from the group consisting of water-soluble polymers and alcohol-soluble polymers (Ingredient B).

The present invention relates also to such cosmetic composition as mentioned above, wherein said mono-$N^\alpha$-acylarginine is represented by the following general formula (1):

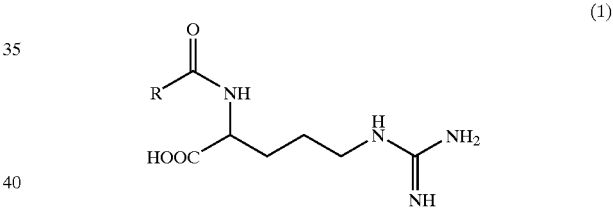

wherein R represents a straight-chain or branched-chain alkyl or alkenyl group having 1–21 carbon atoms.

Moreover, the present invention relates to a cosmetic composition comprising, as active ingredients, one or more members selected from the group consisting of mono-$N^\alpha$-acylarginine crystals which are obtainable by neutralizing an acidic or basic solution of a mixed solvent composed of water and one or more members selected from the group consisting of lower alcohols and polyhydric alcohols, in which mixed solvent a mono-$N^\alpha$-acylarginine has been dissolved, whereby the mono-$N^\alpha$-acylarginine is crystallized, and surface-treated cosmetic powders whose surfaces have been treated with mono-$N^\alpha$-acylarginine crystals (Ingredient A') and one or more members selected from the group consisting of water-soluble polymers and alcohol-soluble polymers (Ingredient B).

Still moreover, the present invention relates to a cosmetic composition such as a hair cosmetic composition, a hair detergent composition, a skin cosmetic composition, or the like, which cosmetic composition comprises, as active ingredients, one or more members selected from the group consisting of mono-$N^\alpha$-acylarginines and crystals thereof, and cosmetic powders whose surfaces have been treated with a mono-$N^\alpha$-acylarginine and/or crystals thereof (Ingredient A") and one or more members selected from the group consisting of water-soluble polymers and alcohol-soluble polymers (Ingredient B).

Further, the present invention relates to a cosmetic composition such as a hair cosmetic composition, a hair detergent composition, a skin cosmetic composition, or the like, which cosmetic composition comprises, as active ingredients, one or more members selected from the group consisting of mono-$N^\alpha$-acylarginines represented by the following general formula (2) and crystals thereof, and cosmetic powders whose surfaces have been treated therewith (Ingredient A''') and one or more members selected from the group consisting of water-soluble polymers and alcohol-soluble polymers (Ingredient B).

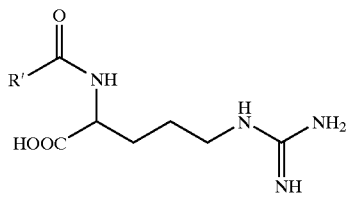
(2)

wherein R' represents a straight-chain or branched-chain alkyl or alkenyl group having 11–15 carbon atoms.

DETAILED DESCRIPTION OF THE INVENTION

Figure 1:
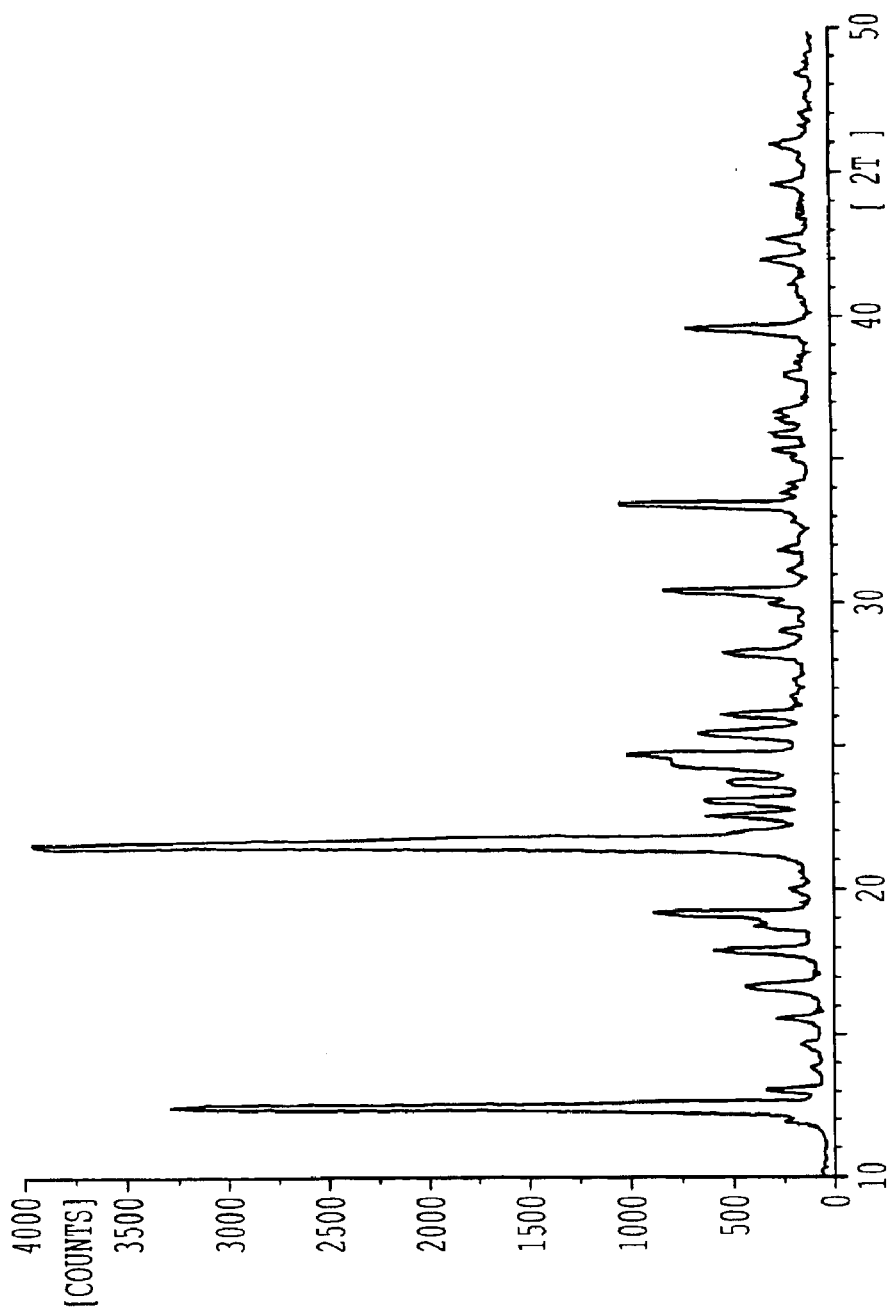
FIG. 1 shows the powder X-ray diffraction pattern of the mono-$N^\alpha$-lauroyl-L-arginine crystals (Compound of Synthetic Example 1).

The present invention will be described below in greater detail.

First, Ingredient A of the inventive cosmetic composition will be described.

The mono-$N^\alpha$-acylarginine to be incorporated in the cosmetic composition of the present invention can be obtained by reacting arginine with a long chain fatty acid halide in a hydrophilic solvent under an alkaline condition (around pH 12) as described in Japanese Patent Application Laid-Open (Kokai) No. 23729/1973 or by heat-dehydrating (i.e., dehydrating by heating) the salt of arginine and a fatty acid at a temperature of 100 to 250° C. as described in Japanese Patent Application Laid-Open (Kokai) No. 1513/1974. Alternatively, as shown in Japanese Patent Application Laid-Open (Kokai) No. 228527/1999, crystals of mono-$N^\alpha$-acylarginine can be obtained by reacting arginine with a long chain fatty acid halide in a mixed solvent of water and a lower alcohol such as methanol, ethanol, propanol, butanol, isopropanol, or t-butanol and/or a polyhydric alcohol such as ethylene glycol, propylene glycol, 1,3-butylene glycol, isoprene glycol, or glycerin, in the presence of an alkali (pH 7 to 13), and converting the reaction mixture into an acidic or basic aqueous solution using an acid or a base, whereby the whole is dissolved well, followed by adjusting the pH to 5 to 7. In the acylation reaction, in the case that the pH upon acylating is lower than 7 or higher than 13, the reaction yield rapidly decreases.

Moreover, the mono-$N^\alpha$-acylarginine to be incorporated in the cosmetic composition of the present invention may exhibit its effects even if it is in the amorphous state, but the crystals thereof obtainable by the above-described methods are preferable particularly in view of conditioning properties such as moist feeling and voluminous feeling for the hair. By the way, amorphous mono-$N^\alpha$-acylarginine may be prepared by the method described in the above-mentioned Japanese Patent Application Laid-Open (Kokai) No. 23729/1973, for example (cf. Synthetic Example 4 described later on).

The mono-$N^\alpha$-acylarginine to be incorporated in the cosmetic composition of the present invention has a straight-chain or branched-chain saturated or unsaturated fatty acid acyl group having 2 to 22 carbon atoms, and examples thereof include mono-$N^\alpha$-acetylarginine, mono-$N^\alpha$-propionylarginine, mono-$N^\alpha$-2-ethylhexanoylarginine, mono-$N^\alpha$-isostearoylarginine, mono-$N^\alpha$-oleoylarginine, mono-$N^\alpha$-octanoylarginine, mono-$N^\alpha$-decanoylarginine, mono-$N^\alpha$-lauroylarginine, mono-$N^\alpha$-myristoylarginine, mono-$N^\alpha$-palmitoylarginine, mono-$N^\alpha$-stearoylarginine, mono-$N^\alpha$-octyldodecylarginine, mono-$N^\alpha$-behenoylarginine, mono-$N^\alpha$-coconut oil fatty acid acylarginine, mono-$N^\alpha$-palm kernel oil fatty acid acylarginine, mono-$N^\alpha$-beef tallow fatty acid acylarginine, and the like. Of these, mono-$N^\alpha$-decanoylarginine, mono-$N^\alpha$-lauroylarginine, mono-$N^\alpha$-myristoylarginine, mono-$N^\alpha$-palmitoylarginine, mono-$N^\alpha$-stearoylarginine, and mono-$N^\alpha$-coconut oil fatty acid acylarginine are preferable in view of feelings upon use for the skin. On the other hand, mono-$N^\alpha$-lauroylarginine, mono-$N^\alpha$-myristoylarginine, mono-$N^\alpha$-palmitoylarginine, and mono-$N^\alpha$-stearoylarginine are particularly excellent in the ability of imparting moist feeling and voluminous feeling to the hair. Of these, particularly preferred are mono-$N^\alpha$-lauroylarginine, mono-$N^\alpha$-myristoylarginine, and mono-$N^\alpha$-palmitoylarginine. Additionally, arginine may be used in any one of D-form, L-form, and DL-form.

Moreover, either wet treatment or dry treatment may be employed as the surface treatment in the preparation of the cosmetic powder whose surfaces have been treated with a mono-$N^\alpha$-acylarginine (hereinafter, sometimes referred to as "surface-treated powder"), which may be incorporated in the cosmetic composition of the present invention solely or in combination with a mono-$N^\alpha$-acylarginine. In the case of wet treatment, the surface-treated powder can be obtained by charging a cosmetic powder (a powder for cosmetics) into an aqueous solution of a strong acid or a strong alkali or an aqueous solution containing an organic solvent such as a lower alcohol, and also dissolving concurrently a mono-$N^\alpha$-acylarginine therein, followed by neutralizing the mixture.

Alternatively, in the case of dry treatment, the surface-treated powder can be obtained by charging a powder to be coated and a mono-N$^\alpha$-acylarginine into a mixing grinder and coating the powder with the mono-N$^\alpha$-acylarginine mechanically at a rotation number of several thousand to several ten thousand r.p.m.

The starting powder (cosmetic powder) usable for the preparation of the surface-treated powder to be incorporated in the cosmetic composition of the present invention is not particularly limited, and examples thereof include organic powders such as nylon powder, polyethylene powder, poly (methyl methacrylate) powder, polystyrene powder, styrene-acrylic acid copolymer resin powder, benzoguanamine resin powder, polytetrafluoroethylene resin powder, cellulose powder, silicone powder and the like; extender pigments such as talc, kaolin, mica, sericite, white mica, phlogopite, synthetic mica, lepidolite, lithia mica, vermiculite, magnesium carbonate, calcium carbonate, aluminum silicate, barium silicate, calcium silicate, magnesium silicate, strontium silicate, tungstic acid metal salt, silica, zeolite, barium sulfate, calcinedcalciumsulfate, calcium phosphate, fluorine apatite, hydroxyapatite, ceramic powder, zinc myristate, calcium palmitate, aluminum stearate, boron nitride and the like; ultraviolet ray-shielding powders such as titanium dioxide, zinc oxide, iron oxide (red iron oxide), iron titanate, fine powdery titanium oxide, needle-shaped titanium oxide, spindle-shaped titanium oxide, rod-shaped titanium oxide, fine powdery zinc oxide, flake-shaped zinc oxide and the like; white and coloring pigments such as γ-iron oxide, yellow iron oxide, black iron oxide, carbon black, mango violet, palto violet, chromium oxide, cerium oxide, chromium hydroxide, cobalt titanate, ultramarine, Prussian blue, titanium oxide-coated mica, titanium oxide-coated bismuth oxychloride, bismuth oxychloride, aluminum powder, copper powder, the Red No. 201 and the like; natural pigments such as chlorophyll, β-carotene and the like; and the like.

The amount of the mono-N$^\alpha$-acylarginine upon the surface treatment of such a cosmetic powder is preferably from 0.01 to 30 parts by weight, more preferably 0.1 to 20 parts by weight, further preferably from 0.5 to 10 parts by weight, relative to 100 parts by weight of the cosmetic powder to be surface-treated in view of effecting the efficient and uniform surface treatment.

The incoporating amount of a mono-N$^\alpha$-acylarginine and/or a cosmetic powder subjected to the surface treatment with a mono-N$^\alpha$-acylarginine is optionally determined depending on the aimed-at product and is not particularly limited, but it is usually from 0.01 to 50 parts by weight, preferably from 0.05 to 10 parts by weight, more preferably from 0.05 to 5 parts by weight based on the total amount of the cosmetic composition.

With regard to these mono-N$^\alpha$-acylarginines and/or cosmetic powders subjected to the surface treatment with a mono-N$^\alpha$-acylarginine, one member selected from these may be used solely, or two or more members may be used in combination.

Next will be explained a water-soluble polymer and/or an alcohol-soluble polymer which constitutes Ingredient B of the cosmetic composition of the present invention.

The water-soluble polymer and alcohol-soluble polymer herein mean anionic, cationic, amphoteric, or nonionic polymers, including no cosmetic silicone compounds, having an average molecular weight of more than 2000, and soluble in water or a lower alcohol such as ethanol or isopropanol. Specific examples thereof include the following.

Examples of the anionic polymers include acrylic acid derivatives such as polyacrylic acid and salts thereof (sodium, potassium, ammonium, triethanolamine, arginine, lysine salts, etc.), acrylic resin, acrylic acid-acrylamide-ethyl acrylate copolymer, and salts thereof, and the like; polyglutamic acid and salts thereof; polyaspartic acid and salts thereof; hyaluronic acid and salts thereof; alginic acid and salts thereof; methacrylic acid derivatives such as alkyl acrylate-alkyl methacrylate-diacetone-acetone acrylamide-methacrylic acid copolymer and salts thereof, polymethacrylic acid and salts thereof, and the like; crotonic acid derivatives such as vinyl acetate-crotonic acid copolymer, crotonic acid-vinyl acetate-vinyl neo-decanoate copolymer, and the like; maleic acid derivatives such as methoxyethylene-maleic anhydride copolymer, isobutylene-maleic acid copolymer, and the like; carboxymethyl cellulose; carboxyvinyl polymers; and the like.

Examples of the cationic polymers include chitin derivatives such as chitosan, partially hydrolyzed chitin, chitosan dl-pyrorridonecarboxylate salt, succinylchitosan, hydroxypropyl chitosan, and the like; dimethyldiallylammonium chloride derivatives such as dimethyldiallylammonium chloride-acrylamide copolymer, polydimethylmethylenepi-peridinium chloride, and the like; cationic celluloses such as O-[2-hydroxy-3-(trimethylammonio)propyl]hydroxyethyl cellulose chloride, O-[2-hydroxy-3-(lauryldimethylammonio)propyl]hydroxyethyl cellulose chloride, and the like; cationic cyamoposis gums such as O-[2-hydroxy-3-(trimethylammonio)propyl cyamoposis gum chloride, and the like; methacrylic acid derivatives such as methacryloylethyldimethyl betaine-methacryloylethyltrimethylammonium chloride-methoxypolyethylene glycol methacrylate copolymer, methacryloylethyldimethyl betaine-methacryloylethyltrimethylammonium chloride-2-hydroxyethyl methacrylate copolymer, diethyl sulfate salt of vinylpyrrolidone-N,N-dimethylaminoethyl methacrylate copolymer, and the like; vinylimidazolinium methochloride-vinylpyrrolidone copolymer; and the like.

Examples of the nonionic polymers include cellulose derivatives such as methyl cellulose, hydroxypropyl methyl cellulose, ethyl cellulose, hydroxyethyl cellulose, hydroxypropyl cellulose, and the like; vinyl derivatives such as polyvinyl alcohol, polyvinylpyrrolidone, polyvinylbutyral, vinylpyrrolidone-styrene copolymer, vinylpyrrolidone-hexadecene copolymer, vinyl acetate-vinylpyrrolidone copolymer, eicosene-vinylpyrrolidone copolymer, and the like; acrylic acid derivatives such as hydroxyethyl acrylate-methoxyethyl acrylate copolymer, hydroxyethyl acrylate-butyl acrylate-methoxyethyl acrylate copolymer, acrylamide-styrene copolymer, alkyl acrylate-styrene copolymer, N-octylacrylamide-acrylic ester copolymer, alkyl acrylates copolymer, N-octylacrylamide-hydroxypropyl acrylate-butylaminoethyl methacrylate, and the like; ethylene glycol derivatives such as polyethylene glycol, highly polymerized polyethylene glycol, and the like; maleic acid derivatives such as vinyl methyl ether-ethyl maleate copolymer, and the like; propylene glycol alginate; polyamide epichlorohydrin resin; polysaccharides and derivatives thereof such as cyamoposis gum, locust bean gum, guince seed, carrageenan, galactan, gum arabic, tragacanth gum, pectin, mannan, starch, xanthane gum, dextran, curdran, succinoglucan, and the like; beef tallow derivatives such as polyoxyethylene beef tallow alkylhydroxymyristylene ether, and the like; sorbitan detrivatives such as polyoxyethylene sorbitan triisostearate; sugar derivatives such as polyoxypropylenemethyl glucoside, polyoxyethylene-dioleatemethyl glucoside, and the like; and the like.

Examples of the amphoteric polymers include copolymers such as acrylamide-acrylic acid-dimethyldiallylammonium chloride copolymer, acrylic acid-dimethyldiallylammonium chloride copolymer, and the like; proteins or hydrolyzed proteins and derivatives thereof such as water-soluble collagen, hydrolyzed keratin and derivatives thereof, hydrolyzed silk and derivatives thereof, hydrolyzed gelatin and derivatives thereof, casein and salts thereof, hydrolyzed casein and derivatives thereof, hydrolyzed conchyolin and derivatives thereof, hydrolyzed albumen and derivatives thereof, soy protein hydrolyzate and derivatives thereof, hydrolyzed wheat protein and derivatives thereof, hydrolyzed elastin and derivatives thereof, albumin, and the like; succinylated carboxymethyl chitosan; and the like.

The water-soluble polymers and alcohol-soluble polymers herein do not include cosmetic silicone compounds as explained above. In the case that a cosmetic silicone oil is employed, sufficient moist feeling cannot be attained for the hair and skin and, in particular, a dry and rough feeling is attained for the hair, so that feelings upon use are not excellent.

Furthermore, the weight-average molecular weight of these water-soluble polymers and alcohol-soluble polymers exceeds 2000. When it is 2000 or less, no sufficient moist feeling is attained for the hair and skin and feelings upon use are not sufficiently excellent.

The incorporating amount of the water-soluble polymer and/or alcohol-soluble polymer to be used in the present invention is optionally determined depending on the aimed-at product and is not particularly limited, but the polymer is usually employed in the range of 0.001 to 50% by weight based on the total amount of the cosmetic composition. Particularly preferred is the range of 0.01 to 10% by weight. When the amount is less than 0.001% by weight, the effects of the present invention can sometimes not be sufficiently exhibited and when it exceeds 50% by weight, hard feeling is imparted to the skin or hair and spreadability sometimes becomes bad.

With regard to these water-soluble polymers and alcohol-soluble polymers, one member selected from them may be employed solely or two or more members in combination.

The mixing ratio (weight ratio) of Ingredient A (or Ingredient A', A", or A''') to Ingredient B is optionally determined depending on the aimed-at product and is not particularly limited, but it may be usually employed in the range of 100:1 to 1:100 parts by weight (i.e., the mixing ratio of (Ingredient A)/(Ingredient B) of 100 to 0.01). Particularly preferred is the range of 30:1 to 1:10 (i.e., the mixing ratio of 30 to 0.1).

The cosmetic composition of the present invention comprising such Ingredient A and B can be used as hair detergents such as shampoo, rinse, rinse-in-shampoo, conditioning shampoo, and the like; various hair cosmetics including hair lotion, hair conditioner, hair treatment, hear cream, hair spray, hair liquid, hair wax, hair water, hair-styling preparation, perming liquid, hair color, acidic hair color, hair manicure, etc.; or various skin cosmetics such as skin lotion, milky lotion, face wash, makeup remover, cleansing lotion, emollient lotion, nourishing cream, emollient cream, massage cream, cleansing cream, body shampoo, hand soap, bar soap, shaving cream, sunburn cosmetics, deodorant powder, deodorant lotion, deodorant spray, makeup removing gel, moisture gel, moisture essence, UV-preventing essence, shaving foam, face powder, foundation, lipstick, cheek rouge, eyeliner, eye shadow, eyebrow pencil, bathing preparation, etc.; mouth detergent such as toothpaste; and the like.

By the way, in addition to the above Ingredients A and B, any other various ordinary additives may be added to the cosmetic composition of the present invention insofar as they do not interfere with the effects of the present invention. Examples thereof include surfactants (anionic surfactants, cationic surfactants, amphoteric surfactants, nonionic surfactants, etc.), waxes, vegetable oils, animal oils and fats, derivatives of natural oils and fats, mineral oils and fats, lower and higher fatty acid esters, synthetic oils and fats (N-acylglutamic acid esters etc.), polymeric substances, alcohols, polyhydric alcohols, extracts (natural perfume materials etc.), amino acids, nucleic acids, vitamins, hydrolyzed proteins and derivatives thereof, glyceryl oleate, enzymes, anti-inflammatory agents, microbicides, antiseptics, anti-oxidants, UV absorbents, chelating agents, sweat retardants, oxidizing dyes, pH regulators, pearly additives, moisturizers, etc., which are raw materials described in Standards of Cosmetic Materials, Specifications for Ingredients of Different Types of Cosmetics, Specifications for Materials of Quasi-drugs, the Japanese Pharmacopoeia, Official Specifications for Food Additives, and the like.

EXAMPLES

The present invention will be described in greater detail with reference to the following examples, but not limited thereto.

<Synthetic Example 1>

Synthesis of Mono-$N^\alpha$-lauroyl-L-arginine Crystals

To 1,106 g of L-arginine were added 6,919 g of isopropyl alcohol and 2,964 g of water. Thereto were concurrently added dropwise 1,522 g of lauroyl chloride (manufactured by Nippon Oil and Fats Co., Ltd.) and 27 wt % NaOH aqueous solution over a period of 2 hours with the pH being maintained at 10.5 to 11.5 and the reaction temperature being maintained at 10 to 13° C. After 1 hour of aging, the reaction mixture was warmed to 50° C. and adjusted to pH 3.8 by adding concentrated hydrochloric acid to dissolve the reaction product completely. Thereafter, the pH was adjusted to 6.0 by adding 27 wt % NaOH aqueous solution to precipitate crystals and the resulting slurry was gradually cooled to 10° C. with stirring. When the slurry was cooled to 10° C., the crystals were collected by filtration and washed with 10 kg of water and 4.4 kg of isopropyl alcohol, successively. The resulting washed crystals were dried under reduced pressure to obtain 2,081 g of mono-$N^\alpha$-lauroyl-L-arginine as flake-shaped crystals (yield 92.3%).

The physical properties of the crystals are shown in the following Table 4.

TABLE 4

| (a) | Decomposition temperature: 159.9° C. (DSC peak). |
| (b) | Powder X-ray diffraction peaks (2θ): 12.49, 21.54, 21.85. |
| (c) | Wave numbers of infrared absorption spectra ($cm^{-1}$): 1683.7, 1654.8, 1625.9, 1544.9, 1471.6, 1461.9, 1446.5, 1407.9. |
| (d) | Elemental analysis (as $C_{18}H_{36}O_3N_4$): |

|  | C | H | O |
| --- | --- | --- | --- |
| Calcd. (%) | 60.64 | 10.17 | 15.72 |
| Found (%) | 60.5 | 10.2 | 15.6 |

Figure 2A:
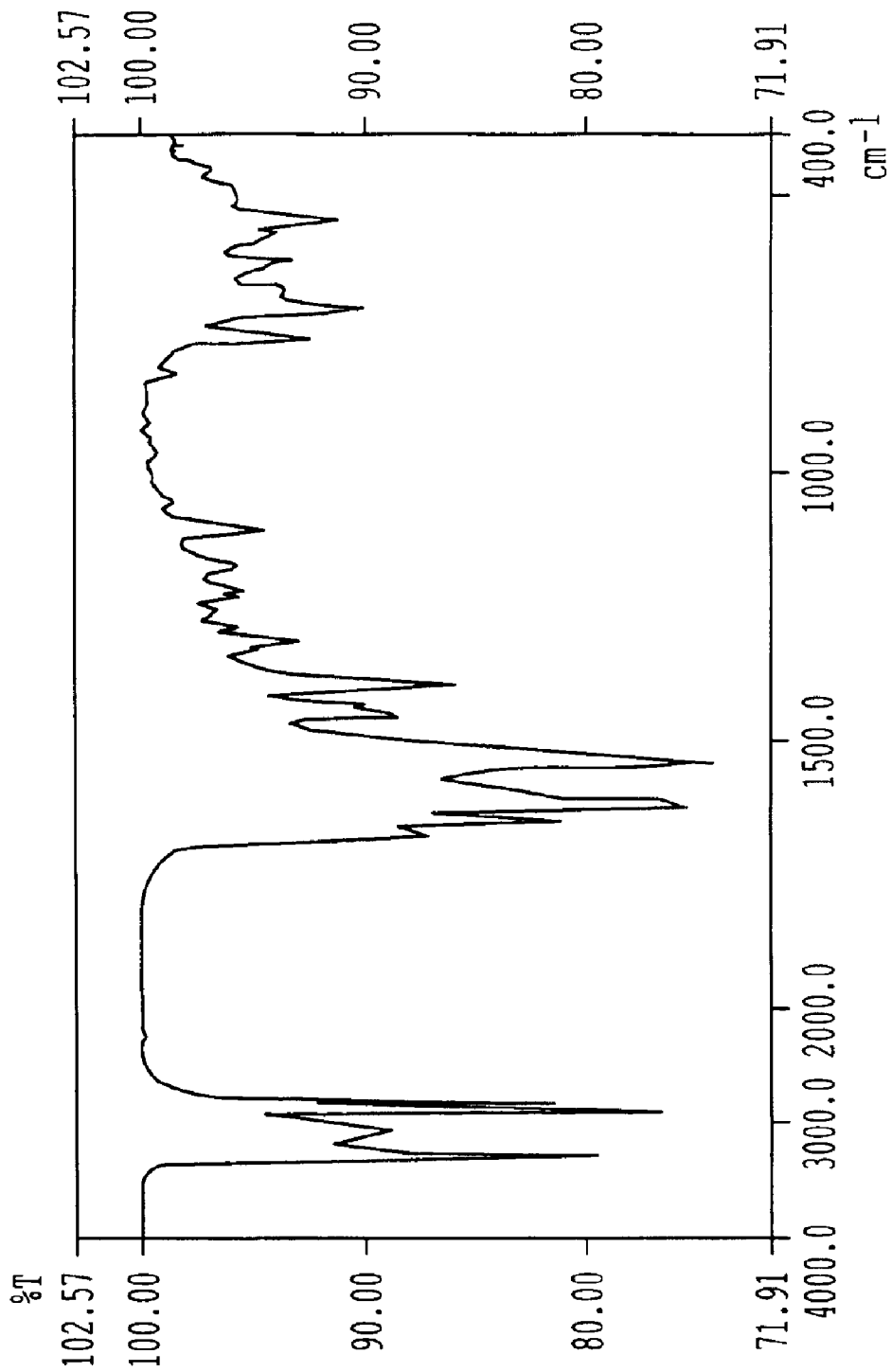
FIGS. 2 (a) and (b) show the infrared absorption spectra (KBr method) of the mono-$N^\alpha$-lauroyl-L-arginine crystals (Compound of Synthetic Example 1).
Figure 2B:
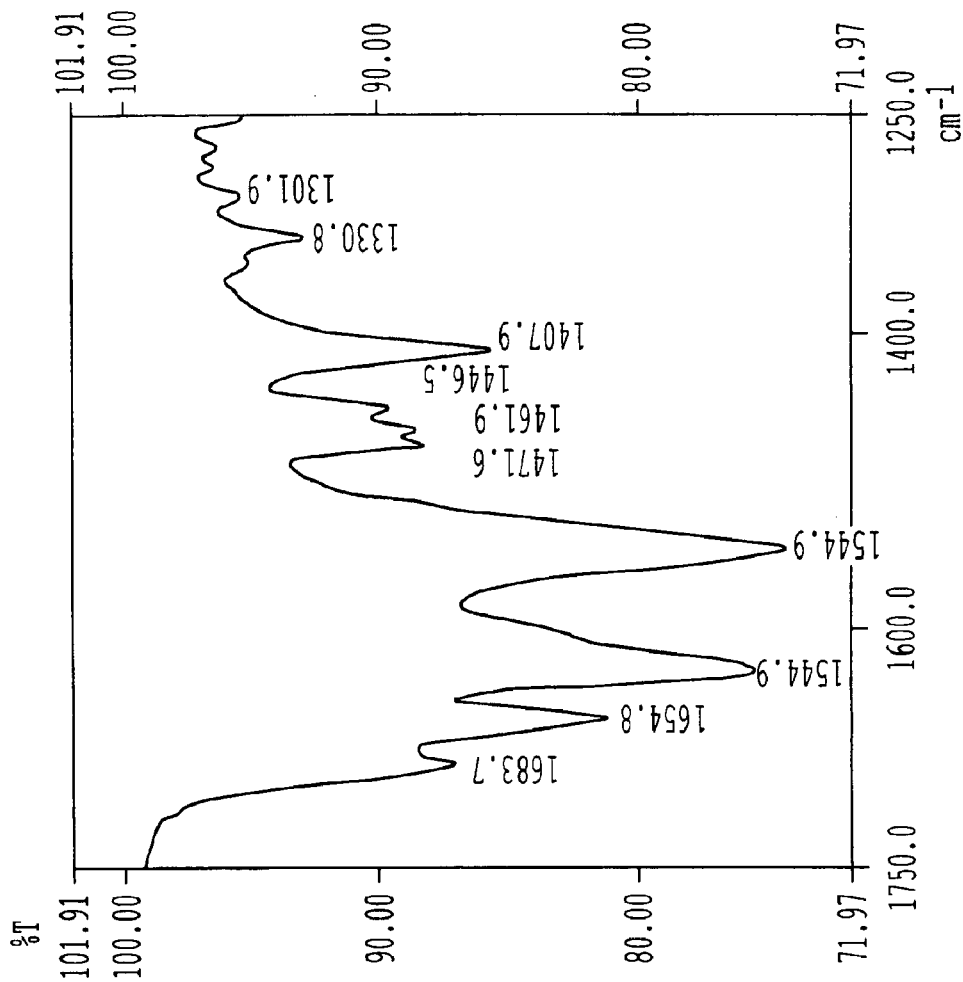

The powder X-ray diffraction pattern of the crystals will be shown in FIG. 1, Infrared absorption spectra (KBr method), in FIG. 2, and the main peaks of the powder X-ray diffraction, in the following Table 5.

TABLE 5

| 2θ | Strength | 2θ | Strength | 2θ | Strength | 2θ | Strength |
|---|---|---|---|---|---|---|---|
| 11.9 | Weak | 21.5 | Strong | 29.0 | Weak | 36.9 | Weak |
| 12.5 | Strong | 21.9 | Strong | 29.9 | Weak | 38.1 | Weak |
| 13.1 | Weak | 22.6 | Medium | 30.3 | Medium | 39.7 | Medium |
| 14.7 | Weak | 23.2 | Medium | 31.2 | Weak | 42.0 | Weak |
| 15.7 | Weak | 23.8 | Medium | 31.9 | Weak | 42.8 | Weak |
| 16.8 | Medium | 24.3 | Medium | 33.4 | Strong | 44.6 | Weak |
| 17.9 | Medium | 24.7 | Medium | 33.9 | Weak | 45.9 | Weak |
| 18.7 | Weak | 25.4 | Medium | 35.4 | Weak | | |
| 19.2 | Medium | 26.1 | Medium | 36.0 | Weak | | |
| 20.0 | Medium | 28.2 | Medium | 36.5 | Weak | | |

<Synthetic Example 2>

Synthesis of Mono-N$^\alpha$-myristoyl-L-arginine Crystals

As in Synthetic Example 1, to 113 g of L-arginine were added 706 g of isopropyl alcohol and 302 g of water. Thereto were concurrently added dropwise 176 g of myristoyl chloride (manufactured by Nippon Oil and Fats Co., Ltd.) and 27 wt % NaOH aqueous solution over a period of 2 hours with the pH being maintained at 10.5 to 11.5 and the reaction temperature, at 10 to 13° C. After 1 hour of aging, the reaction mixture was warmed to 50° C. and adjusted to below pH 2.7 by adding concentrated hydrochloric acid to dissolve the reaction product completely. Thereafter, the pH was adjusted to 6.0 by adding 27 wt % NaOH aqueous solution to precipitate crystals and the resulting slurry was gradually cooled to 10° C. with stirring. When the slurry was cooled to 10° C., the crystals were collected by filtration and washed with 1,500 g of water and 492 g of isopropyl alcohol, successively. The resulting washed crystals were dried under reduced pressure to obtain 230 g of mono-N$^\alpha$-myristoyl-L-arginine as flake-shaped crystals (yield 92.2%).

The physical properties of the crystals are shown in the following Table 6.

TABLE 6

| (a) | Decomposition temperature: 156.2° C. (DSC peak). |
|---|---|
| (b) | Powder X-ray diffraction peaks (2θ): |
| | 11.575, 14.490, 21.700, 31.020, 33.830. |
| (c) | Wave numbers of infrared absorption spectra (cm$^{-1}$): |
| | 1683.7, 1654.8, 1625.9, 1542.9, 1471.6, 1460.0, 1446.5, 1407.9. |

Figure 3:
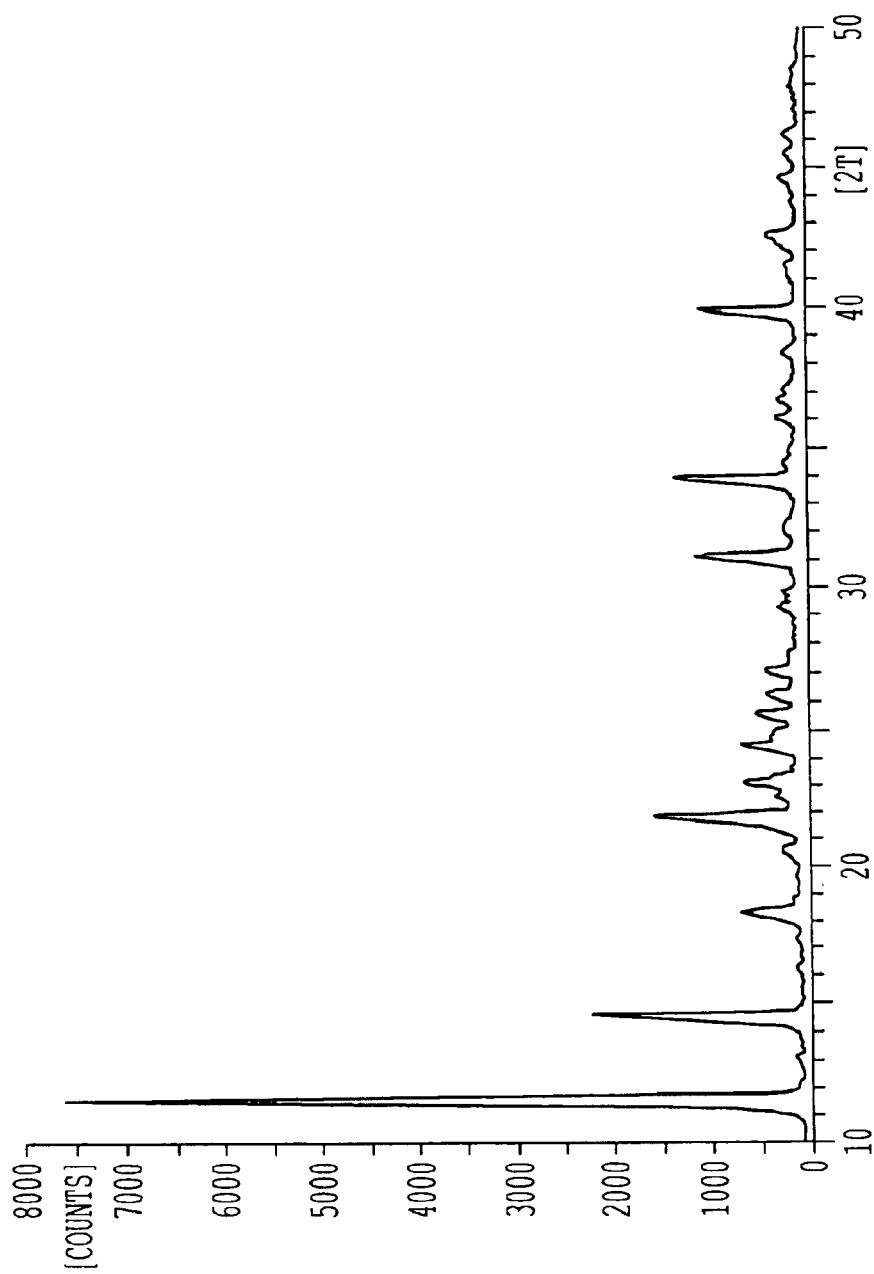
FIG. 3 shows the powder X-ray diffraction pattern of the mono-$N^\alpha$-myristoyl-L-arginine crystals (Compound of Synthetic Example 2).
Figure 4A:
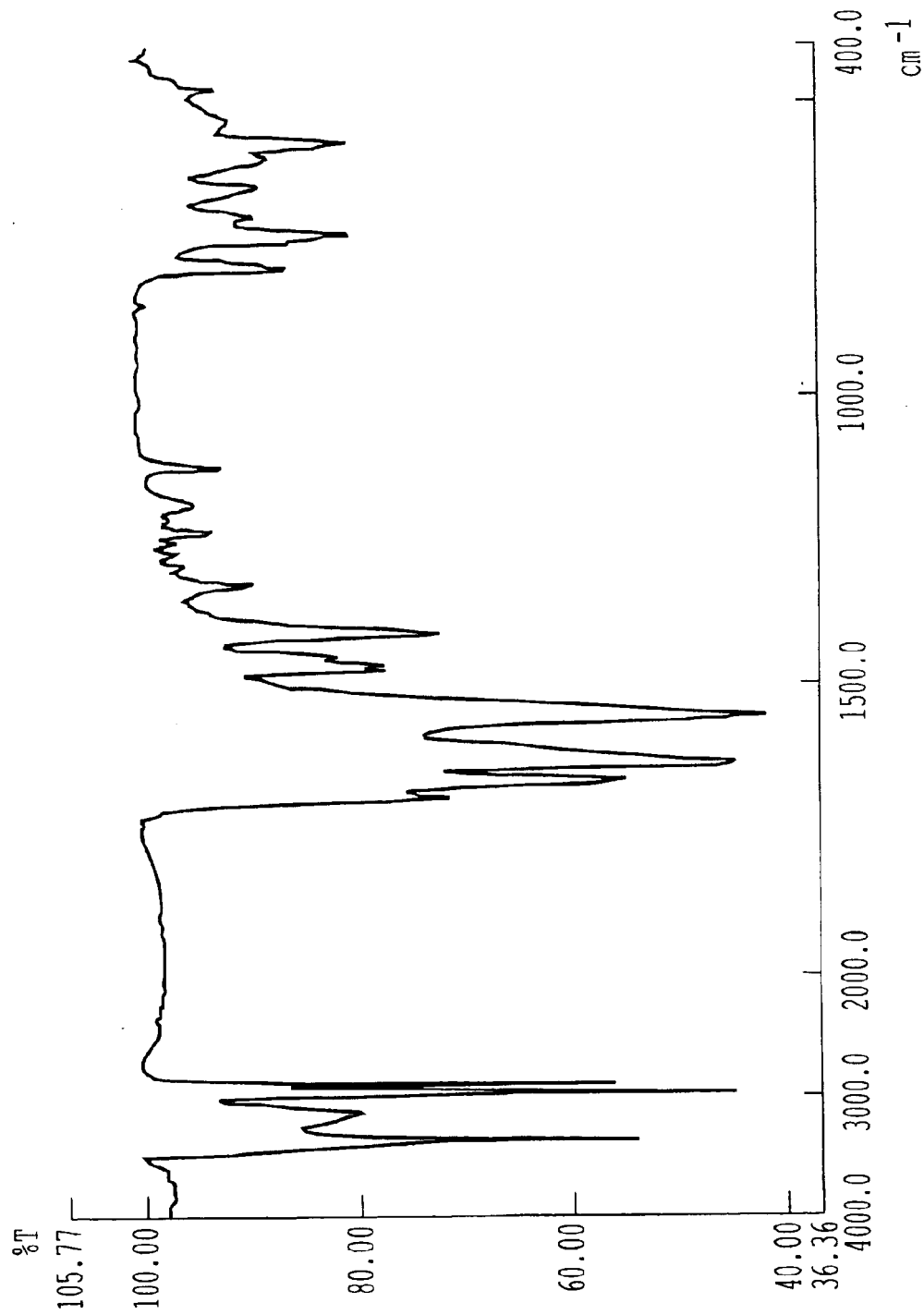
FIGS. 4 (a) and (b) show the infrared absorption spectra (KBr method) of the mono-$N^\alpha$-myristoyl-L-arginine crystals (Compound of Synthetic Example 2).
Figure 4B:
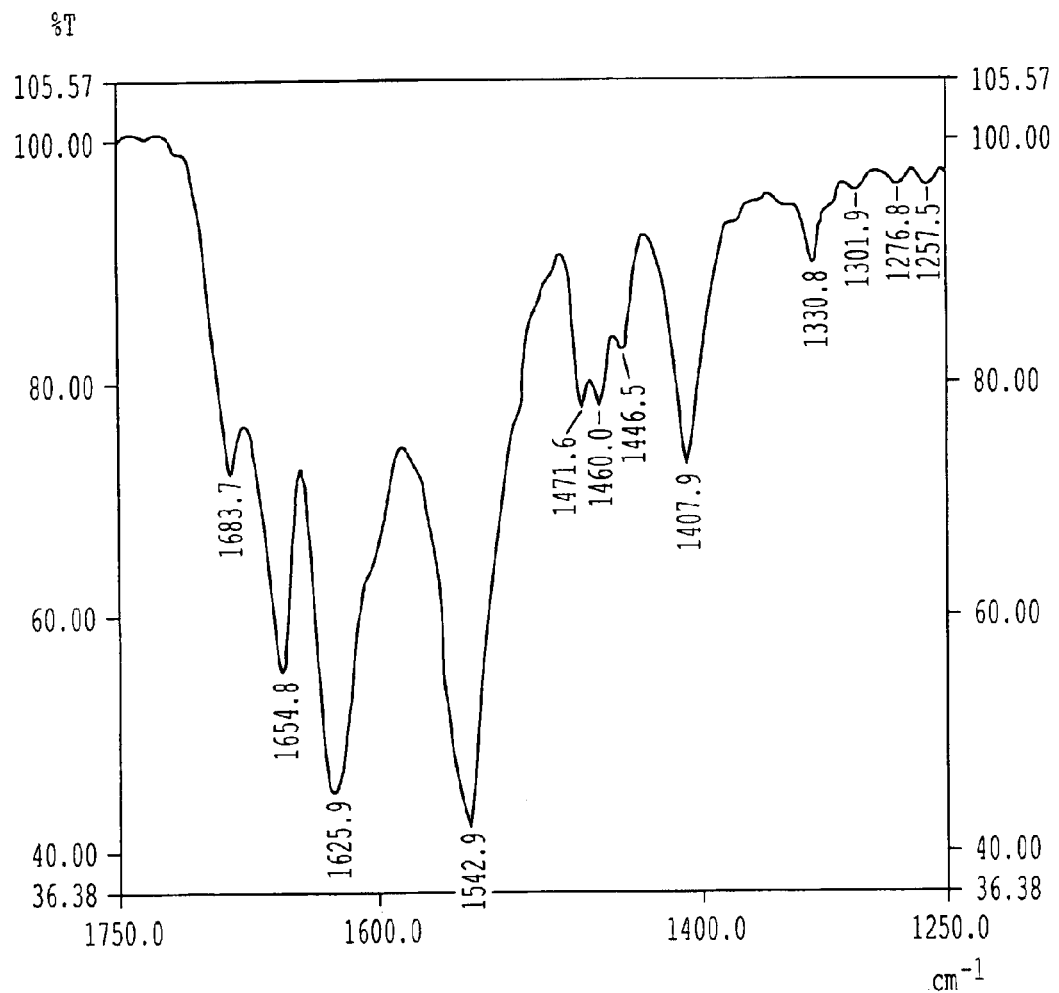

The powder X-ray diffraction pattern of the crystals will be shown in FIG. 3, Infrared absorption spectra (KBr method), in FIG. 4, and the main peaks of the powder X-ray diffraction, in the following Table 7.

TABLE 7

| 2θ | Strength | 2θ | Strength | 2θ | Strength | 2θ | Strength |
|---|---|---|---|---|---|---|---|
| 11.6 | Strong | 24.4 | Medium | 32.1 | Weak | 41.5 | Weak |
| 13.1 | Weak | 25.6 | Medium | 33.8 | Strong | 42.6 | Medium |
| 14.5 | Strong | 26.3 | Medium | 34.5 | Weak | 44.6 | Weak |
| 18.3 | Medium | 27.1 | Medium | 36.0 | Weak | 45.5 | Weak |
| 18.8 | Weak | 27.7 | Weak | 36.7 | Weak | 46.2 | Weak |
| 20.6 | Weak | 29.3 | Weak | 37.1 | Weak | | |

TABLE 7-continued

| 2θ | Strength | 2θ | Strength | 2θ | Strength | 2θ | Strength |
|---|---|---|---|---|---|---|---|
| 21.7 | Strong | 29.8 | Weak | 38.4 | Weak | | |
| 23.0 | Medium | 31.0 | Strong | 39.9 | Medium | | |

<Synthetic Example 3>

Synthesis of Mono-N$^\alpha$-palmitoyl-L-arginine Crystals

As in Synthetic Example 1, to 84.7 g of L-arginine were added 706 g of isopropyl alcohol and 302 g of water. Thereto were concurrently added dropwise 147 g of palmitoyl chloride (manufactured by Aldrich) and 27 wt % NaOH aqueous solution over a period of 2 hours with the pH being at 10.5 to 11.5 and the reaction temperature, at 27 to 30° C. After 1 hour of aging, the reaction mixture was warmed to 50° C. and adjusted to below pH 1.8 by adding concentrated hydrochloric acid to dissolve the reaction product completely. Thereafter, the pH was adjusted to 6.0 by adding 27 wt % NaOH aqueous solution to precipitate crystals and the resulting slurry was gradually cooled to 10° C. with stirring. When the slurry was cooled to 10° C., the crystals were collected by filtration and washed with 1,200 g of water and 320 g of isopropyl alcohol, successively. The resulting washed crystals were dried under reduced pressure to obtain 190 g of mono-N$^\alpha$-palmitoyl-L-arginine as flake-shaped crystals (yield 94.7%).

The physical properties of the crystals are shown in the following Table 8.

TABLE 8

| (a) | Decomposition temperature: 151.5° C. (DSC peak). |
|---|---|
| (b) | Powder X-ray diffraction peaks (2θ): |
| | 10.650, 13.340, 21.590. |
| (c) | Wave numbers of infrared absorption spectra (cm$^{-1}$): |
| | 1683.7, 1654.8, 1625.9, 1542.9, 1471.6, 1460.0, 1448.4, 1407.9. |

Figure 5:
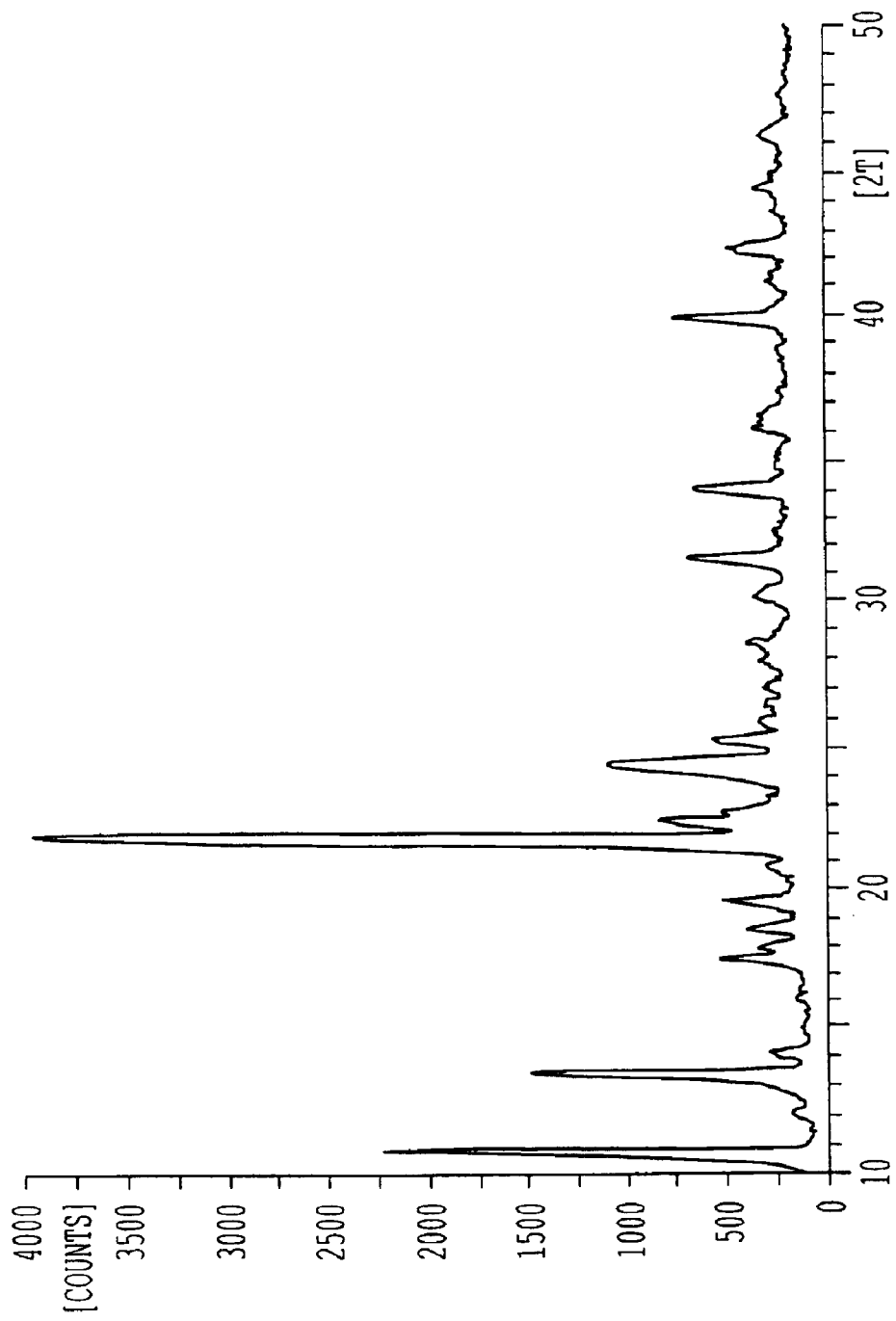
FIG. 5 shows the powder X-ray diffraction pattern of the mono-$N^\alpha$-palmitoyl-L-arginine crystals (Compound of Synthetic Example 3).
Figure 6A:
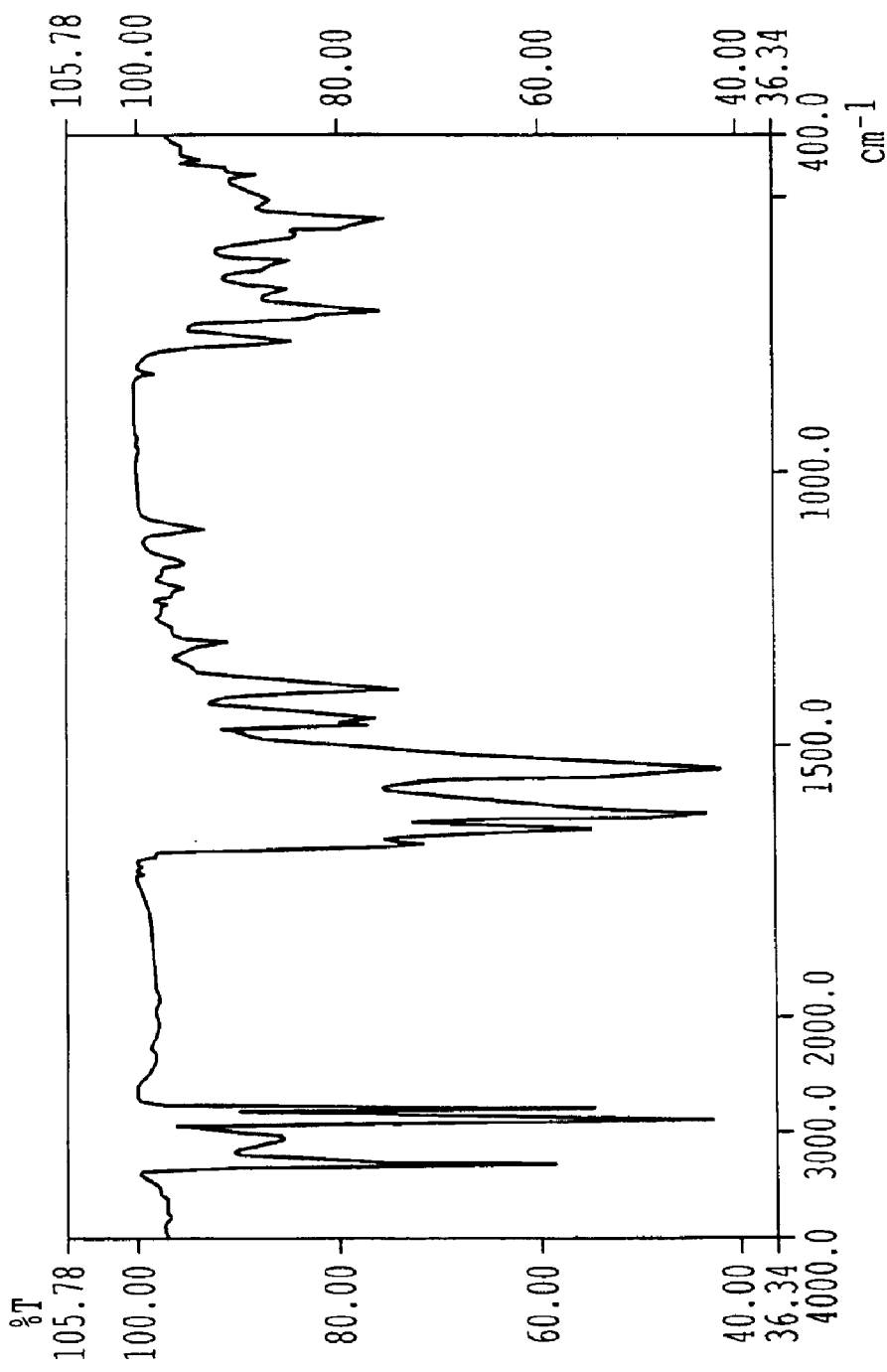
FIGS. 6 (a) and (b) show the infrared absorption spectra (KBr method) of the mono-$N^\alpha$-palmitoyl-L-arginine crystals (Compound of Synthetic Example 3).
Figure 6B:
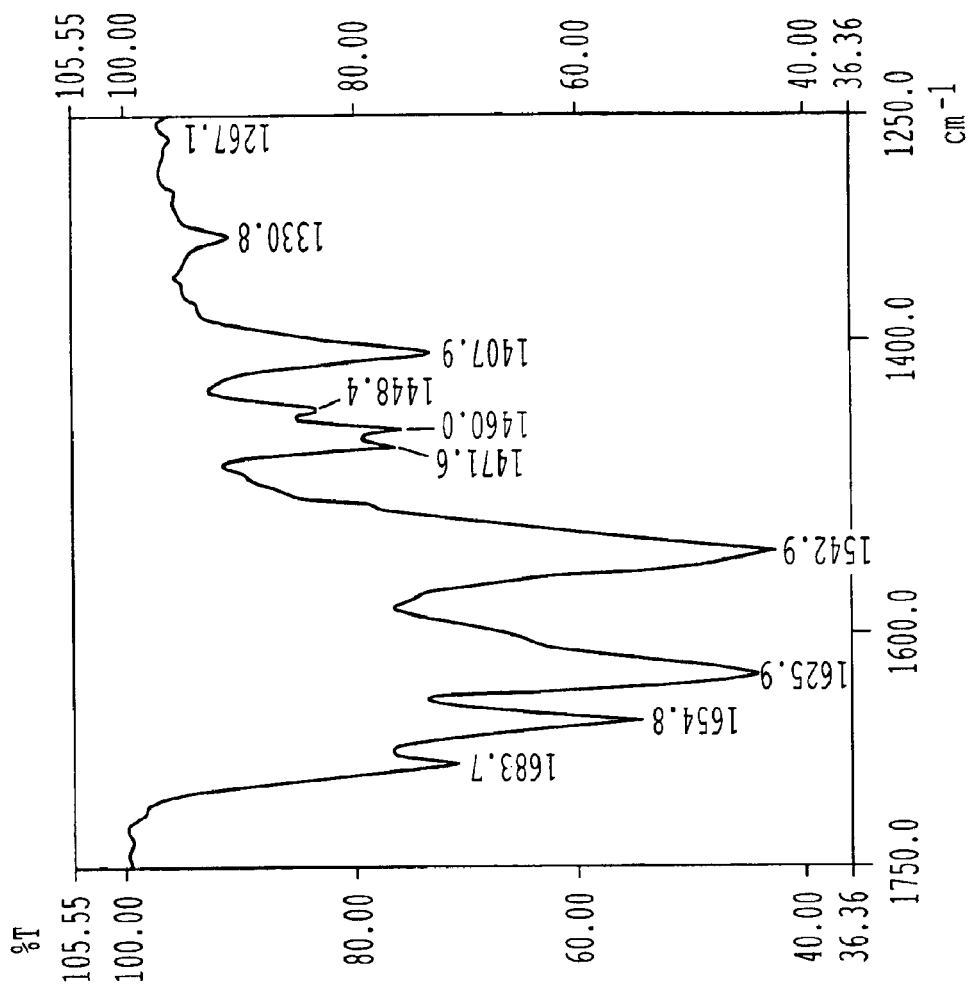

The powder X-ray diffraction pattern of the crystals will be shown in FIG. 5, Infrared absorption spectra (KBr method), in FIG. 6, and the main peaks of the powder X-ray diffraction, in the following Table 9.

TABLE 9

| 2θ | Strength | 2θ | Strength | 2θ | Strength | 2θ | Strength |
|---|---|---|---|---|---|---|---|
| 10.7 | Strong | 20.8 | Weak | 27.0 | Weak | 36.6 | Weak |
| 12.1 | Weak | 21.6 | Strong | 27.9 | Weak | 39.8 | Medium |
| 13.3 | Strong | 22.4 | Medium | 28.5 | Weak | 42.2 | Weak |
| 14.1 | Weak | 22.8 | Medium | 30.1 | Weak | 44.4 | Weak |
| 17.4 | Medium | 24.3 | Medium | 31.5 | Medium | 46.3 | Weak |
| 17.9 | Weak | 25.2 | Medium | 32.5 | Weak | | |
| 18.6 | Weak | 25.9 | Weak | 34.1 | Medium | | |
| 19.5 | Medium | 26.4 | Weak | 36.0 | Weak | | |

<Synthetic Example 4>

Synthesis of Mono-N$^\alpha$-lauroyl-L-arginine (amorphous)

In accordance with the method of Example 1 in the above-mentioned Japanese Patent Application Laid-Open (Kokai) No. 23729/1973, mono-N$^\alpha$-lauroyl-L-arginine was synthesized.

To 35.0 g of L-arginine were added 118.7 g of acetone and 200 g of water. Thereto were concurrently added dropwise 36.5 g of lauroyl chloride ("lauroyl chloride" manufactured by Nippon Oil and Fats Co., Ltd.) and 45 ml of 8N NaOH aqueous solution over a period of 2 hours with the pH being maintained at 11.5 to 12.0 and the reaction temperature being maintained at 15 to 25° C. After 2 hours of aging, the reaction mixture was adjusted to pH 5.0 with 6N sulfuric acid with cooling and then poured into about 300 ml of ice-water to precipitate crude crystals of mono-$N^\alpha$-lauroyl-L-arginine, which were collected by filtration and then dried (yield 55 g). The crude crystals were washed by stirring in 300 ml of petroleum benzine and then filtered, and the crystals were dried under reduced pressure to obtain 51 g of mono-$N^\alpha$-lauroyl-L-arginine (yield 85%).

The physical properties of the crystals are shown in the following Table 10.

TABLE 10

| | |
|---|---|
| (a) | Decomposition temperature: 116.6° C. (DSC peak). |
| (b) | Powder X-ray diffraction peaks (2θ): 21.56 |
| (c) | Wave numbers of infrared absorption spectra (cm$^{-1}$): 1653.2, 1630.0, 1543.2, 1471.9, 1462.2, 1448.7, 1408.2. |
| (d) | Elemental analysis (as $C_{18}H_{36}O_3N_4$): |

| | C | H | O |
|---|---|---|---|
| Calcd. (%) | 60.64 | 10.17 | 15.72 |
| Found (%) | 59.72 | 10.31 | 15.04 |

Figure 7:
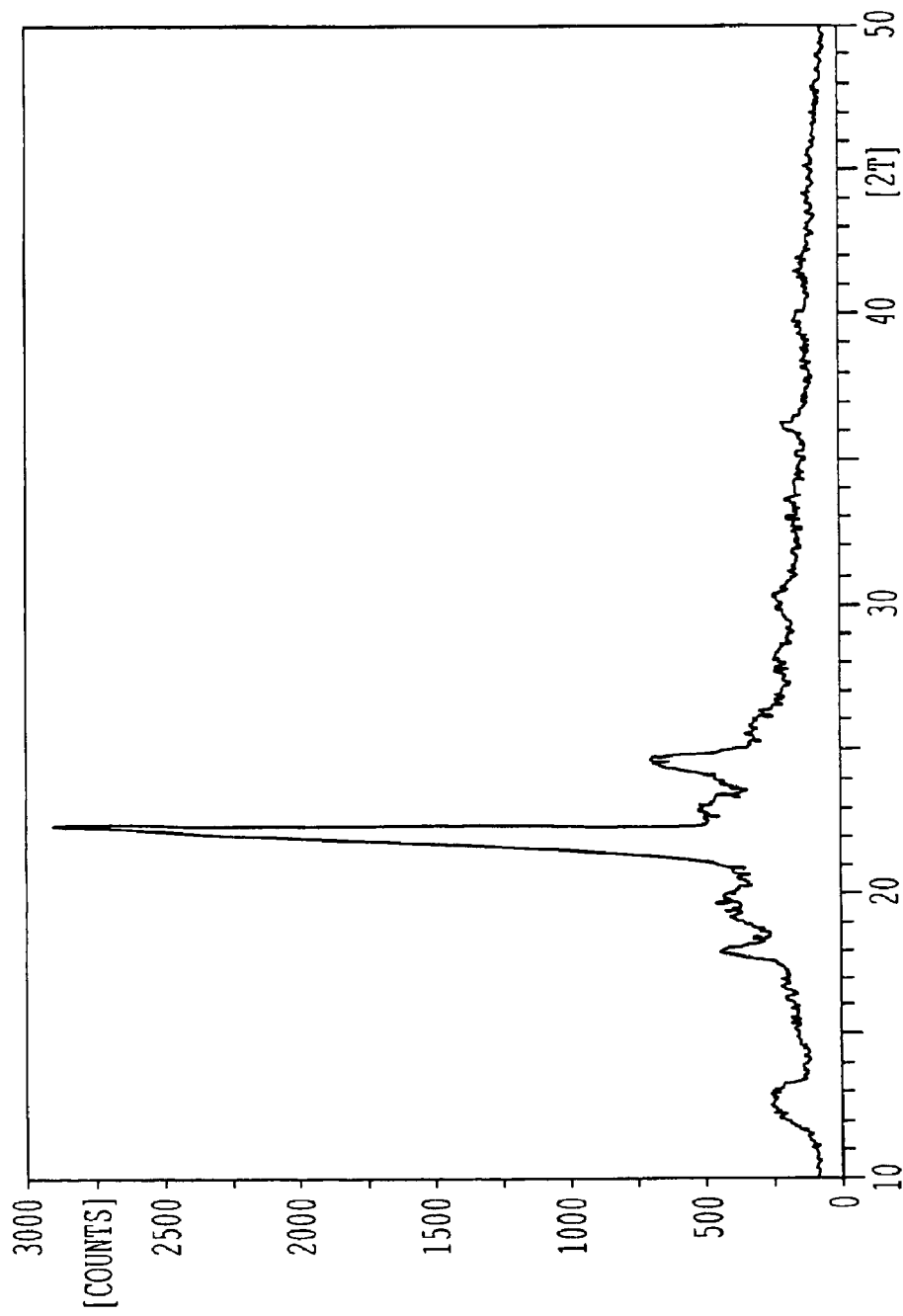
FIG. 7 shows the powder X-ray diffraction pattern of the mono-$N^\alpha$-lauroyl-L-arginine (Compound of Synthetic Example 4).
Figure 8A:
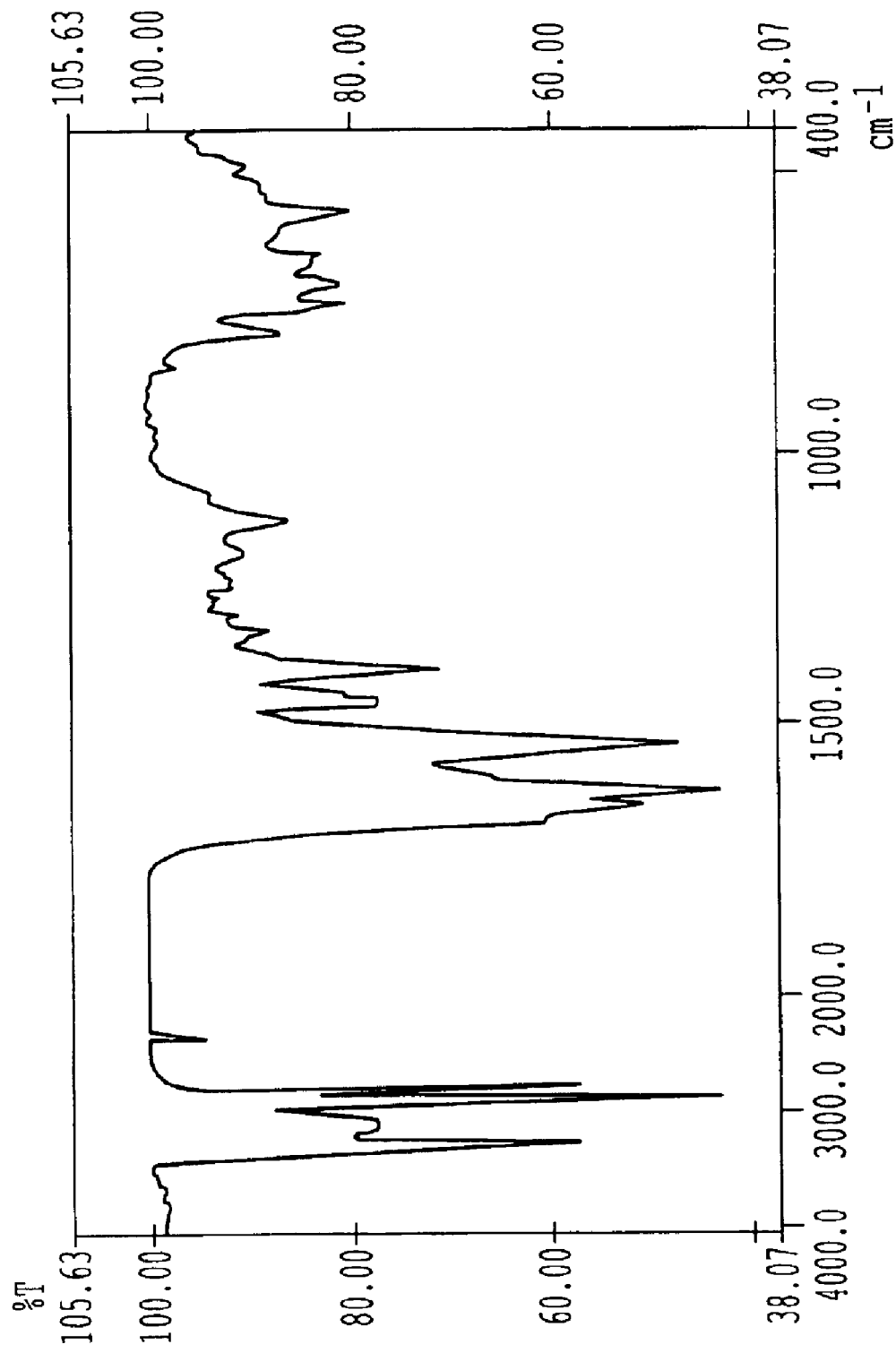
FIGS. 8 (a) and (b) show the infrared absorption spectra (KBr method) of the mono-$N^\alpha$-lauroyl-L-arginine (Compound of Synthetic Example 4).
Figure 8B:
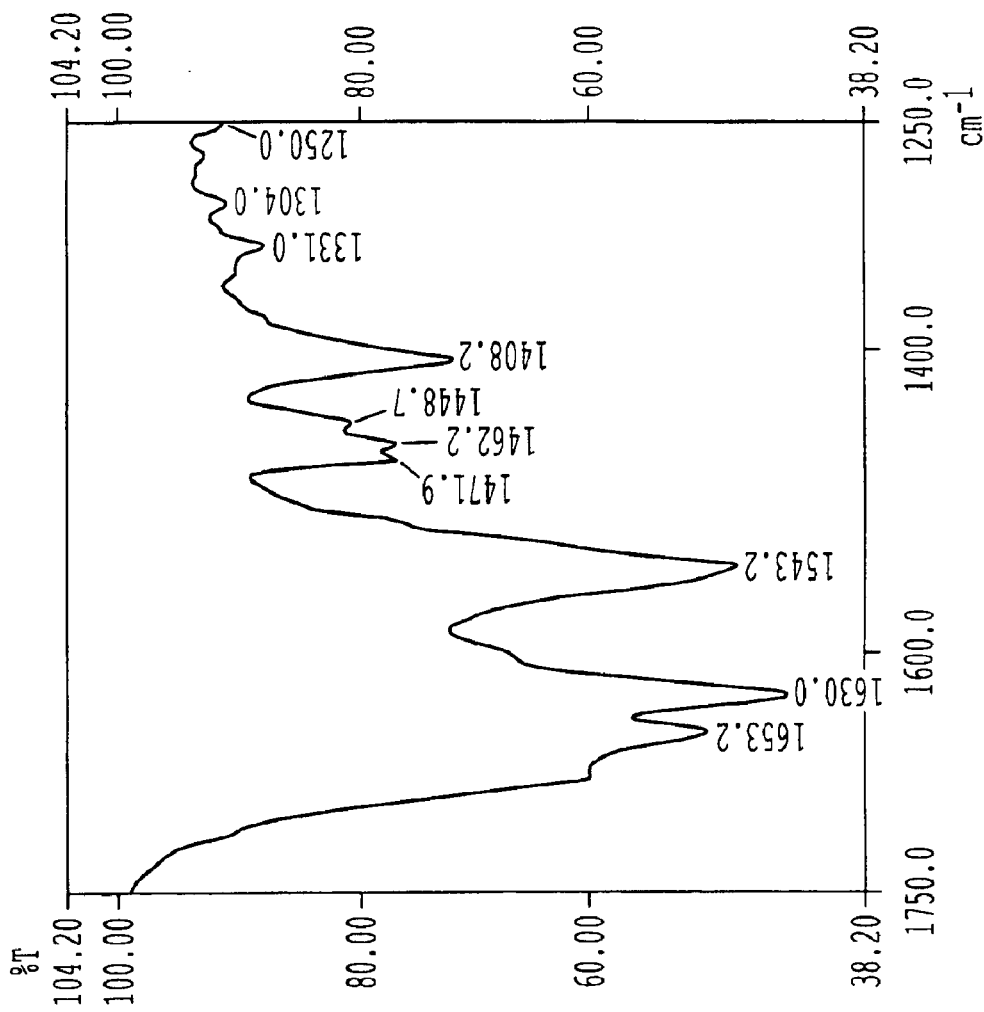

The powder X-ray diffraction pattern thereof will be shown in FIG. 7, Infrared absorption spectra (KBr method), in FIG. 8, and the main peaks of the powder X-ray diffraction, in the following Table 11.

TABLE 11

| 2θ | Strength | 2θ | Strength | 2θ | Strength |
|---|---|---|---|---|---|
| 13.0 | Weak | 19.0 | Weak | 22.9 | Weak |
| 17.8 | Weak | 21.6 | Strong | 24.5 | Weak |

Characteristic peaks as shown in the case of the mono-$N^\alpha$-lauroyl-L-arginine obtained in Synthetic Example 1 were not observed in the powder X-ray diffraction chart of the mono-$N^\alpha$-lauroyl-L-arginine obtained in the present Synthetic Example and, in this sense, the present compound can be said to be amorphous.

By the way, mono-$N^\alpha$-decanoylarginine, mono-$N^\alpha$-stearoylarginine, and mono-$N^\alpha$-coconut oil fatty acid acylarginine were also produced under almost the same reaction conditions.

<Surface-treatment Example 1>

Surface Treatment of Talc With $N^\alpha$-lauroyl-L-arginine

A surface-treated powder was obtained by conducting surface treatment by mixing 5.0 g of talc as a cosmetic powder ("Microace P-30", manufactured by Nippon Talc Co., Ltd.) and 0.25 g of the compound obtained in Synthetic Example 1 and mixing them with stirring for 1 minute twice using a home mixer ("IFM-150" manufactured by Iwatani Sangyo K. K.).

<Test Example 1>

Shampoo

Shampoos having each composition (expressed by wt %, 100% in total) shown in the following Table 13 were prepared in the usual manner (four kinds of Examples and 1 kind of Comparative Example). These shampoos were each applied to a bundle of the hair which had been washed with 1% aqueous solution of sodium lauryl ether sulfate, and then the hair was thoroughly washed with water. After drying, a sensory evaluation was conducted by a panel of five expert panelists with respect to (a) moist feeling of the hair and (b) voluminous feeling of the hair. The evaluation was carried out through the steps of calculating an average value on the basis of the evaluation standard shown in the following Table 12 and rating the case of the average value of 4 or higher as very good (◎), the case of the value of 3.5 to 3.9 as good (○), the case of the value of 3 to 3.5 as moderate (Δ), and the case of the value of 2.9 or lower as bad (X). The evaluation results are also shown in Table 13.

TABLE 12

| | <Evaluation Standard> |
|---|---|
| (a) | Moist feeling after drying<br>5: Strong moist feeling<br>4: Moist feeling<br>3: Moderate<br>2: Weak Moist feeling<br>1: No moist feeling |
| (b) | Voluminous feeling after drying<br>5: Strong voluminous feeling<br>4: Voluminous feeling<br>3: Moderate<br>2: Weak voluminous feeling<br>1: No voluminous feeling |

TABLE 13

| Component | Example 1 | Example 2 | Example 3 | Example 4 | Comparative Example 1 |
|---|---|---|---|---|---|
| $N^\alpha$-Lauroyl-L-arginine (of Synthetic Example 1) | 1.5 | | | | |
| $N^\alpha$-Lauroyl-L-arginine (of Synthetic Example 4) | | | 1.5 | | |
| $N^\alpha$-Palmitoyl-L-arginine (of Synthetic Example 3) | | 1.5 | | | |
| $N^\alpha$-Stearoyl-L-arginine | | | | 1.5 | |
| Cationic cellulose (*1) | 0.2 | 0.2 | 0.2 | 0.2 | 0.2 |
| Sodium lauryl ether sulfate | 11 | 11 | 11 | 11 | 11 |

TABLE 13-continued

| Component | Example 1 | Example 2 | Example 3 | Example 4 | Comparative Example 1 |
|---|---|---|---|---|---|
| Cocoamide propyl betain | 3 | 3 | 3 | 3 | 3 |
| Citric acid monohydrate | 0.05 | 0.05 | 0.05 | 0.05 | 0.05 |
| Water | Barance | Barance | Barance | Barance | Barance |
| Moist feeling after drying | ⊚ | ⊚ | ○ | ⊚ | X |
| Voluminous feeling after drying | ⊚ | ⊚ | ○ | ○ | X |

(*1) "Polymer JR400" manufactured by Amerchol CO., Ltd.

<Test Example 2>

Milky Lotion

Milky lotions having each composition shown in the following Table 15 (expressed by wt %, 100% in total) were prepared (six kinds of Examples and three kind of Comparative Examples). A suitable amount of each milky lotion was applied to the back of hands. A sensory evaluation was conducted by a panel of five expert panelists with respect to (a) smoothening property upon use, (b) moist feeling after use, (c) sticky feeling after use, and (d) occlusive feeling after use. The evaluation was carried out through the steps of calculating an average value on the basis of the evaluation standard shown in the following Table 14 and rating the case of the average value of 4 or higher as very good (⊚), the case of the value of 3.5 to 3.9 as good (○), the case of the value of 3 to 3.5 as moderate (Δ), and the case of the value of 2.9 or lower as bad (X). The evaluation results are also shown in Table 15.

TABLE 14

| <Evaluation Standard> | |
|---|---|
| (a) | Smoothening property after use |
| | 5: Smoothening |
| | 4: Slight Smoothening |
| | 3: Moderate |
| | 2: Weak Smoothening |
| | 1: No smoothening |
| (b) | Moist feeling after use |
| | 5: Strong moist feeling |
| | 4: Moist feeling |
| | 3: Moderate |
| | 2: Weak Moist feeling |
| | 1: No moist feeling |
| (c) | Sticky feeling after use |
| | 5: No sticky feeling |
| | 4: Weak sticky feeling |
| | 3: Moderate |
| | 2: Slight sticky feeling |
| | 1: Sticky feeling |
| (d) | Occlusive feeling after use |
| | 5: No occlusive feeling |
| | 4: Weak occlusive feeling |
| | 3: Moderate |
| | 2: Slight occlusive feeling |
| | 1: Occlusive feeling |

TABLE 15

| Component | Example 5 | Example 6 | Example 7 | Example 8 | Example 9 | Example 10 | Comparative Example 2 | Comparative Example 3 | Comparative Example 4 |
|---|---|---|---|---|---|---|---|---|---|
| N$^\alpha$-Lauroyl-L-arginine (of Synthetic Example 1) | 1 | | | 1 | | | | | |
| N$^\alpha$-Lauroyl-L-arginine (of Synthetic Example 4) | | 1 | | | | | | | |
| N$^\alpha$-Palmitoyl-L-arginine (of Synthetic Example 3) | | | 1 | | 1 | | | | |
| Talc treated with N$^\alpha$-lauroyl-L-arginine (of Surface-treatment Example 1) | | | | | | 5 | | | |
| N$^\alpha$-Lauroyl-L-lysine | | | | | | | | | 1 |
| Carboxyvinyl polymer (*1) (1 wt % aqueous solution) | 10 | 10 | 10 | | | | 10 | | 10 |
| NaOH (10 wt % aqueous solution) | 0.4 | 0.4 | 0.4 | | | | 0.4 | | 0.4 |
| Xanthan gum (1% aqueous solution) | | | | 10 | 10 | 10 | | 10 | |
| Liquid paraffin | 8 | 8 | 8 | 8 | 8 | 8 | 8 | 8 | 8 |
| Cetanol | 1 | 1 | 1 | 1 | 1 | 1 | 1 | 1 | 1 |
| Glyceryl stearate | 2 | 2 | 2 | 2 | 2 | 2 | 2 | 2 | 2 |
| Sorbitan POE(20) monooleate | 4 | 4 | 4 | 4 | 4 | 4 | 4 | 4 | 4 |
| Propylene glycol | 3 | 3 | 3 | 3 | 3 | 3 | 3 | 3 | 3 |
| 1,3-Butylene glycol | 5 | 5 | 5 | 5 | 5 | 5 | 5 | 5 | 5 |
| Methylparaben | 0.2 | 0.2 | 0.2 | 0.2 | 0.2 | 0.2 | 0.2 | 0.2 | 0.2 |
| Water | 65.4 | 65.4 | 65.4 | 65.8 | 65.8 | 61.8 | 66.4 | 66.8 | 65.4 |
| Smoothening property | ⊚ | ○ | ⊚ | ⊚ | ⊚ | ⊚ | X | X | ○ |

TABLE 15-continued

| Component | Example 5 | Example 6 | Example 7 | Example 8 | Example 9 | Example 10 | Comparative Example 2 | Comparative Example 3 | Comparative Example 4 |
|---|---|---|---|---|---|---|---|---|---|
| after use | | | | | | | | | |
| Moist feeling after use | ◎ | ○ | ◎ | ◎ | ◎ | ○ | Δ | Δ | Δ |
| Sticky feeling after use | ◎ | ◎ | ◎ | ◎ | ◎ | ◎ | Δ | Δ | Δ |
| Occlusive feeling after use | ◎ | ◎ | ◎ | ◎ | ◎ | ◎ | X | X | Δ |

(*1) B F Goodrich "Carbopol 940"

There will be given below Preparation Examples of cosmetic compositions of the present invention.

<Preparation of Shampoo>

Three kinds of shampoos having each formulation shown in the following Table 16 were prepared in the usual manner.

TABLE 16

Shampoo

| Ingredient | Example 11 | Example 12 | Example 13 |
|---|---|---|---|
| Ingredient A of the invention | | | |
| $N^\alpha$-Lauroyl-L-arginine (of Synthetic Example 1) | 0.1 | | |
| $N^\alpha$-Cocoyl-L-arginine | | 0.1 | |
| $N^\alpha$-Palmitoyl-L-arginine (of Synthetic Example 3) | | | 0.1 |
| Ingredient B of the invention | | | |
| Cationic cellulose (*1) | 0.1 | | |
| Dimethyldiallylammonium chloride-acrylamide copolymer (*2) | 0.3 | | |
| Cationic cellulose (*3) | | 0.2 | |
| Polydimethyl-methylenepiperidinium chloride (*4) | | | 0.3 |
| Other ingredients | | | |
| Sodium lauryl ether sulfate | 10.0 | 10.0 | 10.0 |
| Coconut oil fatty acid diethanolamide | 3.0 | 3.0 | 3.0 |
| Concentrated glycerin | 2.0 | 2.0 | 2.0 |
| Antiseptic | Suitable amount | Suitable amount | Suitable amount |
| Water | Balance | Balance | Balance |

(*1) "Leoguard GP" manufactured by Lion Corp.
(*2) "Lipoflow MN" manufactured by Lion Corp.
(*3) "LM-200" manufactured by Amerchol Co., Ltd.
(*4) "Merquat 100" manufactured by Calgon Co.

All the shampoos prepared were excellent in conditioning effects such as moist feeling and voluminous feeling after drying for the hair.

<Preparation of Hair-treatment>

Three kinds of Hair treatment having each formulation shown in the following Table 17 were prepared in the usual manner.

TABLE 17

Hair treatment

| Ingredient | Example 14 | Example 15 | Example 16 |
|---|---|---|---|
| Ingredient A of the invention | | | |
| $N^\alpha$-Lauroyl-L-arginine (of Synthetic Example 1) | 0.3 | | |
| $N^\alpha$-Cocoyl-L-arginine | | 0.3 | |
| $N^\alpha$-Palmitoyl-L-arginine (of Synthetic Example 3) | | | 0.3 |
| Ingredient B of the invention | | | |
| Hydroxyethyl cellulose (*1) | 0.1 | 0.1 | 0.1 |
| Other ingredients | | | |
| Silicone oil | 3.0 | 3.0 | 3.0 |
| Liquid paraffin | 1.0 | 1.0 | 1.0 |
| Cetyl alcohol | 1.5 | 1.5 | 1.5 |
| Stearyl alcohol | 1.0 | 1.0 | 1.0 |
| Stearyltrimethyl ammonium chloride | 0.7 | 0.7 | 0.7 |
| Glycerol | 3.0 | 3.0 | 3.0 |
| Antiseptic | Suitable amount | Suitable amount | Suitable amount |
| Water | Balance | Balance | Balance |

(*1) Aqalon "NATROSOL 250 HHR"

All the hair treatments prepared were excellent in conditioning effects such as moist feeling and voluminous feeling after drying for the hair.

<Preparation of Hair-styling Gel>

Three kinds of hair-styling gel having each formulation shown in the following Table 18 were prepared in the usual manner.

TABLE 18

Hair-styling gel

| Ingredient | Example 17 | Example 18 | Example 19 |
|---|---|---|---|
| Ingredient A of the invention | | | |
| $N^\alpha$-Lauroyl-L-arginine (of Synthetic Example 1) | 0.2 | | |
| $N^\alpha$-Cocoyl-L-arginine | | 0.2 | |
| $N^\alpha$-Palmitoyl-L-arginine (of Synthetic Example 3) | | | 0.2 |
| Ingredient B of the invention | | | |
| Polyvinyl pyrrolidone (*1) | 2.0 | 2.0 | 2.0 |
| Carboxyvinyl polymer (*2) | 1.0 | 1.0 | 1.0 |
| Other ingredients | | | |
| Polyoxyethylene(24)cholesteryl ether | 1.0 | 1.0 | 1.0 |
| triethanolamine | 1.0 | 1.0 | 1.0 |

TABLE 18-continued

Hair-styling gel

| Ingredient | Example 17 | Example 18 | Example 19 |
|---|---|---|---|
| Antiseptic | Suitable amount | Suitable amount | Suitable amount |
| Water | Balance | Balance | Balance |

(*1) ISP "PVP K"
(*2) B F Goodrich "Carbopol 980"

All the hair-styling gels prepared were excellent in conditioning effects such as moist feeling and voluminous feeling after drying for the hair.

<Preparation of Hair Manicure>

Three kinds of hair manicures having each formulation shown in the following Table 19 were prepared in the usual manner.

TABLE 19

Hair-manicure

| Ingredient | Example 20 | Example 21 | Example 22 |
|---|---|---|---|
| Ingredient A of the invention | | | |
| $N^{\alpha}$-Lauroyl-L-arginine (of Synthetic Example 1) | 0.5 | | |
| $N^{\alpha}$-Cocoyl-L-arginine | | 0.5 | |
| $N^{\alpha}$-Palmitoyl-L-arginine (of Synthetic Example 3) | | | 0.5 |
| Ingredient B of the invention | | | |
| Xanthane gum | 3.0 | 3.0 | 3.0 |
| Other ingredients | | | |
| Benzyl alcohol | 10.0 | 10.0 | 10.0 |
| Cetanol | 0.2 | 0.2 | 0.2 |
| Polyoxyethylene(2)cetyl ether | 0.5 | 0.5 | 0.5 |
| Liquid paraffin | 3.0 | 3.0 | 3.0 |
| Black 401 | 0.5 | 0.5 | 0.5 |
| Water | Balance | Balance | Balance |

All the hair-manicures prepared were excellent in conditioning effects such as moist feeling and voluminous feeling after drying for the hair.

<Preparation of Skin Lotion>

Three kinds of skin lotions having each formulation shown in Table 20 were prepared in the usual manner.

TABLE 20

Skin lotion

| Ingredient | Example 23 | Example 24 | Example 25 |
|---|---|---|---|
| Ingredient A of the invention | | | |
| $N^{\alpha}$-Lauroyl-L-arginine (of Synthetic Example 1) | 0.1 | | |
| $N^{\alpha}$-Cocoyl-L-arginine | | 0.1 | |
| $N^{\alpha}$-Palmitoyl-L-arginine (of Synthetic Example 3) | | | 0.1 |
| Ingredient B of the invention | | | |
| Hydroxypropyl cellulose (*1) | 0.1 | 0.1 | 0.1 |
| Other ingredients | | | |
| Polyoxyethylene(15) glyceryl monostearate | 1.0 | 1.0 | 1.0 |
| Propylene glycol | 1.0 | 1.0 | 1.0 |
| Liquid paraffin | 0.2 | 0.2 | 0.2 |

TABLE 20-continued

Skin lotion

| Ingredient | Example 23 | Example 24 | Example 25 |
|---|---|---|---|
| Antiseptic | Suitable amount | Suitable amount | Suitable amount |
| Water | Balance | Balance | Balance |

(*1) Sin-Etsu Chemical Co., Ltd. "HPC"

All the skin lotions prepared were excellent in feelings upon use such as smoothening property, moist feeling and the like without sticky feeling and occlusive feeling for the skin.

<Preparation of Beauty Lotion>

Three kinds of beauty lotions having each formulation shown in Table 21 were prepared in the usual manner.

TABLE 21

Skin lotion

| Ingredient | Example 26 | Example 27 | Example 28 |
|---|---|---|---|
| Ingredient A of the invention | | | |
| $N^{\alpha}$-Lauroyl-L-arginine (of Synthetic Example 1) | 0.4 | | |
| $N^{\alpha}$-Cocoyl-L-arginine | | 0.4 | |
| $N^{\alpha}$-Palmitoyl-L-arginine (of Synthetic Example 3) | | | 0.4 |
| Ingredient B of the invention | | | |
| Hydroxypropyl-methylcellulose (*1) | 0.3 | 0.3 | 0.3 |
| Other ingredients | | | |
| Polyoxyethylene(10)cetyl ether | 2.0 | 2.0 | 2.0 |
| Glyceryl monostearate | 2.0 | 2.0 | 2.0 |
| Stearic acid | 3.0 | 3.0 | 3.0 |
| Cetanol | 1.0 | 1.0 | 1.0 |
| Liquid paraffin | 5.0 | 5.0 | 5.0 |
| 2-Ethylhexyl stearate | 3.0 | 3.0 | 3.0 |
| Triethanolamine | 1.0 | 1.0 | 1.0 |
| Antiseptic | Suitable amount | Suitable amount | Suitable amount |
| Water | Balance | Balance | Balance |

(*1) Sin-Etsu Chemical Co., Ltd. "Metolose 65SH4000"

All the beauty lotions prepared were excellent in feelings upon use such as smoothening property, moist feeling and the like without sticky feeling and occlusive feeling for the skin.

<Preparation of Pack>

Three kinds of packs having each formulation shown in Table 20 were prepared in the usual manner.

TABLE 22

Pack

| Ingredient | Example 29 | Example 30 | Example 31 |
|---|---|---|---|
| Ingredient A of the invention | | | |
| $N^{\alpha}$Lauroyl-L-arginine (of Synthetic Example 1) | 1.0 | | |
| $N^{\alpha}$-Cocoyl-L-arginine | | 1.0 | |
| $N^{\alpha}$-Palmitoyl-L-arginine (of Synthetic Example 3) | | | 1.0 |

TABLE 22-continued

| | Pack | | |
|---|---|---|---|
| Ingredient | Example 29 | Example 30 | Example 31 |
| Ingredient B of the invention | | | |
| Polyvinyl alcohol (35–45 cps) | 6.0 | 6.0 | 6.0 |
| Polyvinyl alcohol (20–25 cps) | 7.0 | 7.0 | 7.0 |
| Other ingredients | | | |
| Ethanol | 20.0 | 20.0 | 20.0 |
| Polyoxyethylene(20)sorbitan monolaurate | 0.1 | 0.1 | 0.1 |
| Antiseptic | Suitable amount | Suitable amount | Suitable amount |
| Water | Balance | Balance | Balance |

All the packs prepared were excellent in feelings upon use such as smoothening property, moist feeling and the like without sticky feeling and occlusive feeling for the skin.

<Preparation of Transparent Shampoo>

One kind of transparent shampoo having the formulation shown in Table 23 was prepared in the usual manner.

TABLE 23

| | Transparent shampoo |
|---|---|
| Ingredient | Example 32 |
| Ingredient A of the invention | |
| $N^\alpha$-Lauroyl-L-arginine (of Synthetic Example 1) | 0.5 |
| Ingredient B of the invention | |
| Hydroxypropyl trimethylammonium chloride guar gum (*1) | 0.15 |
| Other ingredients | |
| Sodium lauryl ether sulfate (*2) | 10.8 |
| Lauric acid monoisopanol amide | 1.0 |
| Coconut oil fatty acid amide propylbetaine | 2.2 |
| Concentrated glycerol | 1.0 |
| Citric acid | 0.05 |
| Methyl paraben | 0.2 |
| Sodium benzoate | 0.2 |
| Water | Balance |

(*1) "Jaguar C162" ex Rhodia
(*2) "Texapon HS" ex Henkel

The transparent shampoo prepared was excellent in conditioning effects such as moist feeling and voluminous feeling after drying for the hair.

[Effects of the Invention]

According to the present invention, there can be easily provided cosmetic compositions excellent in conditioning effects such as moist feeling and voluminous feeling in the case of hair cosmetics and excellent in feelings upon use such as smoothening property and moist feeling without sticky feeling and occlusive feeling in the case of skin cosmetics.

What is claimed is:

1. A cosmetic composition, comprising, as active ingredients:
   (A) one or more members selected from the group consisting of (a) mono-$N^\alpha$-acylarginines and (b) cosmetic powders which have been surface-treated with a mono-$N^\alpha$-acylarginines; and
   (B) 0.01 to 10% by weight, based on the total weight of said composition, of one or more members selected from the group consisting of water-soluble polymers and alcohol-soluble polymers, each having a weight average molecular weight of more than 2,000, provided said water-soluble polymers and said alcohol-soluble polymers are not a silicone compound.

2. The cosmetic composition according to claim 1, wherein said mono-$N^\alpha$-acylarginine is represented by the following formula (1):

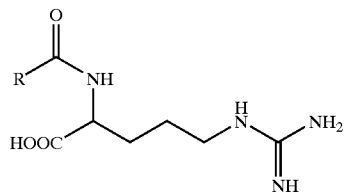

(1)

wherein R represents a straight-chain or branched-chain alkyl or alkenyl group having 1–21 carbon atoms.

3. The cosmetic composition according to claim 1, wherein said mono-$N^\alpha$-acylarginine is in the form of crystals obtainable by neutralizing an acidic or basic solution of a mixed solvent, said mixed solvent comprising water and one or more members selected from the group consisting of lower alcohols and polyhydric alcohols, in which said solvent a mono-$N^\alpha$-acylarginine has been dissolved, whereby said mono-$N^\alpha$-acylarginine is crystallized.

4. The cosmetic composition according to claim 1, wherein said mono-$N^\alpha$-acylarginine is mono-$N^\alpha$-lauroyl-L-arginine crystals, which exhibit:
   (a) powder X-ray diffraction peaks (2θ) at 12.5°, 21.5°, and 21.9°; and
   (b) an infrared absorption spectrum with absorption peaks at wave numbers (cm$^{-1}$) 1684, 1655, 1626, 1545, 1472, 1462, 1447, and 1408.

5. The cosmetic composition according to claim 1, wherein said mono-$N^\alpha$-acylarginine is mono-$N^\alpha$-myristoyl-L-arginine crystals, which exhibit:
   (a) powder X-ray diffraction peaks (2θ) at 11.6°, 14.5°, 21.7°, 31.0°, and 33.8°; and
   (b) an infrared absorption spectrum with absorption peaks at wave numbers (cm$^{-1}$) 1684, 1655, 1626, 1543, 1472, 1460, 1447, and 1408.

6. The cosmetic composition according to claim 1, wherein said mono-$N^\alpha$-acylarginine is mono-$N^\alpha$-palmitoyl-L-arginine crystals, which exhibit:
   (a) powder X-ray diffraction peaks (2θ) at 10.7°, 13.3°, and 21.6°; and
   (b) an infrared absorption spectrum with absorption peaks at wave numbers (cm$^{-1}$) 1684, 1655, 1626, 1543, 1472, 1460, 1448, and 1408.

7. The cosmetic composition according to claim 1, wherein said cosmetic composition is a hair cosmetic composition.

8. The cosmetic composition according to claim 1, wherein said cosmetic composition is a hair detergent composition.

9. The cosmetic composition according to claim 1, wherein said cosmetic composition is a skin cosmetic composition.

10. The cosmetic composition according to claim 1, wherein said mono-$N^\alpha$-acylarginine is represented by the following formula (2):

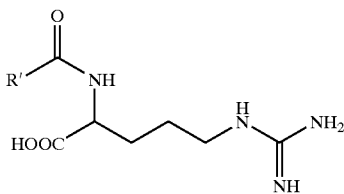

(2)

wherein R' represents a straight-chain or branched-chain alkyl or alkenyl group having 11–15 carbon atoms.

11. The cosmetic composition according to claim 1, comprising a mono-$N^{\alpha}$-acylarginine selected from the group consisting of mono-$N^{\alpha}$-acetylarginine, mono-$N^{\alpha}$-propionylarginine, mono-$N^{\alpha}$-2-ethylhexanoylarginine, mono-$N^{\alpha}$-isostearoylarginine, mono-$N^{\alpha}$-oleoylarginine, mono-$N^{\alpha}$-octanoylarginine, mono-$N^{\alpha}$-decanoylarginine, mono-$N^{\alpha}$-lauroylarginine, mono-$N^{\alpha}$-myristoylarginine, mono-$N^{\alpha}$-palmitoylarginine, mono-$N^{\alpha}$-stearoylarginine, mono-$N^{\alpha}$-octyldodecylarginine, mono-$N^{\alpha}$-behenoylarginine, mono-$N^{\alpha}$-coconut oil fatty acid acylarginine, mono-$N^{\alpha}$-palm kernel oil fatty acid acylarginine, and mono-$N^{\alpha}$-beef tallow fatty acid acylarginine.

12. The cosmetic composition according to claim 1, comprising a cosmetic powder which has been surface-treated with a mono-$N^{\alpha}$-acylarginine, wherein said cosmetic powder is selected from the group consisting of organic powders, extender pigments, ultraviolet ray-shielding powders, white and coloring pigments, and natural pigments.

13. The cosmetic composition according to claim 1, comprising a water-soluble polymer.

14. The cosmetic composition according to claim 13, wherein said water-soluble polymer is selected from the group consisting of anionic polymers, cationic polymers, amphoteric polymers, and nonionic polymers.

15. The cosmetic composition according to claim 1, comprising an alcohol-soluble polymer.

16. The cosmetic composition according to claim 15, wherein said alcohol-soluble polymer is selected from the group consisting of anionic polymers, cationic polymers, amphoteric polymers, and nomonic polymers.

17. The cosmetic composition according to claim 1, which comprises 0.01 to 50% by weight, based on the total weight of said composition, of (A) one or more members selected from the group consisting of (a) mono-$N^{\alpha}$-acylarginines and (b) cosmetic powders which have been surface-treated with a mono-$N^{\alpha}$-acylarginine.

18. The cosmetic composition according to claim 1, which comprises: (A) one or more members selected from the group consisting of (a) mono-$N^{\alpha}$-acylarginines and (b) cosmetic powders which have been surface-treated with a mono-$N^{\alpha}$-acylarginines; and (B) one or more members selected from the group consisting of water-soluble polymers and alcohol-soluble polymers in a ratio of 100:1 to 1:100 parts by weight, of (A) to (B).

19. The cosmetic composition according to claim 1, which comprises: (A) one or more members selected from the group consisting of(a) mono-$N^{\alpha}$-acylarginines and (b) cosmetic powders which have been surface-treated with a mono-$N^{\alpha}$-acylarginine; and (B) one or more members selected from the group consisting of water-soluble polymers and alcohol-soluble polymers in a ratio of 30:1 to 1:10 parts by weight, of (A) to (B).

* * * * *